(12) United States Patent
McGillicuddy

(10) Patent No.: US 11,576,659 B2
(45) Date of Patent: Feb. 14, 2023

(54) BONE MARROW ASPIRATION DEVICE AND METHOD

(71) Applicant: Cervos Medical LLC, Marshfield, MA (US)

(72) Inventor: Andrew McGillicuddy, Humarock, MA (US)

(73) Assignee: Cervos Medical LLC, Marshfield, MA (US)

( * ) Notice: Subject to any disclaimer, the term of this patent is extended or adjusted under 35 U.S.C. 154(b) by 355 days.

(21) Appl. No.: 16/817,777

(22) Filed: Mar. 13, 2020

(65) Prior Publication Data

US 2020/0205792 A1 Jul. 2, 2020

Related U.S. Application Data

(62) Division of application No. 14/885,821, filed on Oct. 16, 2015, now Pat. No. 10,993,707.
(Continued)

(51) Int. Cl.
 *A61B 10/02* (2006.01)
(52) U.S. Cl.
 CPC .... *A61B 10/025* (2013.01); *A61B 2010/0258* (2013.01)
(58) Field of Classification Search
 CPC ...................... A61B 10/025; A61B 2010/0258
 See application file for complete search history.

(56) References Cited

U.S. PATENT DOCUMENTS

| 3,893,445 A | 7/1975 | Hofsess |
| 4,010,737 A | 3/1977 | Vilaghy et al. |

(Continued)

FOREIGN PATENT DOCUMENTS

| WO | WO 2006/027549 A1 | 3/2006 |
| WO | WO 2010/138895 A3 | 2/2010 |

(Continued)

OTHER PUBLICATIONS

Notice of Allowance, U.S. Appl. No. 17/080,999 entitled "Bone Marrow Aspiration Device and Method," dated Feb. 5, 2021.
(Continued)

*Primary Examiner* — Dung T Ulsh
(74) *Attorney, Agent, or Firm* — Hamilton, Brook, Smith & Reynolds, P.C.

(57) ABSTRACT

A bone marrow aspiration device and related method includes an introducer assembly and an aspiration assembly to couple to the introducer assembly. The introducer assembly includes an introducer cannula having a proximal end and a distal end. The introducer cannula defines a lumen between the distal and proximal ends, the distal end being configured to penetrate bone of a patient. The aspiration assembly includes an aspiration cannula that is receivable in the lumen of the introducer cannula and that extends beyond the distal end of the introducer cannula. The aspiration cannula includes a port to aspirate bone marrow, the port being distal to the distal end of the introducer cannula. The aspiration device further includes a mechanism at the introducer assembly to move the introducer cannula and the aspiration cannula in tandem relative to a distal end of the mechanism when the aspiration cannula is positioned within bone.

19 Claims, 18 Drawing Sheets

Related U.S. Application Data

(60) Provisional application No. 62/174,849, filed on Jun. 12, 2015, provisional application No. 62/065,409, filed on Oct. 17, 2014.

(56) References Cited

U.S. PATENT DOCUMENTS

| | | |
|---|---|---|
| 4,249,541 A | 2/1981 | Pratt |
| 4,262,676 A | 4/1981 | Jamshidi |
| 4,356,828 A | 11/1982 | Jamshidi |
| 4,366,822 A | 1/1983 | Altshuler |
| 4,469,109 A | 9/1984 | Mehl |
| 4,487,209 A | 12/1984 | Mehl |
| 4,630,616 A | 12/1986 | Tretinyak |
| 4,649,918 A | 3/1987 | Pegg et al. |
| 4,793,363 A | 12/1988 | Ausherman et al. |
| 4,838,282 A | 6/1989 | Strasser et al. |
| 5,026,350 A | 6/1991 | Tanaka et al. |
| 5,027,827 A | 7/1991 | Code et al. |
| 5,279,306 A | 1/1994 | Mehl |
| 5,331,972 A | 7/1994 | Wadhwani et al. |
| 5,357,974 A | 10/1994 | Baldridge |
| 5,368,046 A * | 11/1994 | Scarfone ............... A61B 10/025 604/117 |
| 5,429,138 A | 7/1995 | Jamshidi |
| 5,522,398 A | 6/1996 | Goldenberg et al. |
| 5,526,821 A | 6/1996 | Jamshidi |
| 5,807,275 A | 7/1998 | Jamshidi |
| 5,807,276 A | 9/1998 | Russin |
| 5,833,628 A | 11/1998 | Yuan et al. |
| 5,954,671 A | 9/1999 | O'Neill |
| 6,007,496 A | 12/1999 | Brannon |
| 6,063,037 A | 5/2000 | Mittermeier et al. |
| 6,080,115 A | 6/2000 | Rubinstem |
| 6,090,121 A | 7/2000 | Weber et al. |
| 6,110,128 A | 8/2000 | Andelin et al. |
| 6,264,618 B1 | 7/2001 | Landi et al. |
| 6,302,852 B1 | 10/2001 | Fleming et al. |
| 6,312,394 B1 | 11/2001 | Fleming |
| 6,416,484 B1 | 7/2002 | Miller et al. |
| 6,425,887 B1 | 7/2002 | McGuckin et al. |
| 6,478,751 B1 | 11/2002 | Krueger et al. |
| 6,554,778 B1 | 4/2003 | Fleming |
| 6,554,803 B1 | 4/2003 | Ashman |
| 6,730,043 B2 | 5/2004 | Krueger et al. |
| 6,755,793 B2 | 6/2004 | Lamoureux et al. |
| 6,849,051 B2 | 2/2005 | Sramek et al. |
| 6,905,489 B2 | 6/2005 | Mantell et al. |
| 6,916,292 B2 | 7/2005 | Morawski et al. |
| 6,981,948 B2 | 1/2006 | Pellegrino et al. |
| 7,081,123 B2 | 7/2006 | Merboth et al. |
| 7,179,232 B2 | 2/2007 | Sutton et al. |
| 7,278,972 B2 | 10/2007 | Lamoureux et al. |
| 7,462,181 B2 | 12/2008 | Kraft et al. |
| 7,637,872 B1 | 12/2009 | Fox |
| 7,850,651 B2 | 12/2010 | Allee et al. |
| 8,043,253 B2 | 10/2011 | Kraft et al. |
| 8,343,133 B2 | 1/2013 | Allee et al. |
| 9,017,298 B2 | 4/2015 | Allee et al. |
| 9,226,732 B2 | 1/2016 | Azimpoor et al. |
| 10,231,716 B2 | 3/2019 | McGillicuddy et al. |
| 10,556,046 B2 | 2/2020 | McGillicuddy |
| 10,568,661 B2 | 2/2020 | McGillicuddy |
| 10,993,707 B2 | 5/2021 | McGillicuddy |
| 11,039,817 B2 | 6/2021 | McGillicuddy |
| 2001/0001811 A1 | 5/2001 | Burney et al. |
| 2003/0050574 A1 | 3/2003 | Krueger |
| 2004/0077973 A1 | 4/2004 | Groenke et al. |
| 2004/0127814 A1 | 7/2004 | Negroni |
| 2004/0153005 A1 * | 8/2004 | Krueger ............... A61B 10/025 600/571 |
| 2004/0191897 A1 | 9/2004 | Muschler |
| 2004/0267154 A1 | 12/2004 | Sutton et al. |
| 2006/0247552 A1 | 11/2006 | Ikehara et al. |
| 2006/0276747 A1 | 12/2006 | Moos |
| 2007/0016100 A1 | 1/2007 | Miller |
| 2007/0055282 A1 | 3/2007 | Muschler |
| 2007/0066987 A1 | 3/2007 | Scanlan et al. |
| 2007/0198043 A1 | 8/2007 | Cox et al. |
| 2007/0293788 A1 | 12/2007 | Entrekin et al. |
| 2008/0045857 A1 | 2/2008 | Miller et al. |
| 2008/0214957 A1 | 9/2008 | Verra et al. |
| 2009/0149774 A1 | 6/2009 | Simon et al. |
| 2010/0069843 A1 | 3/2010 | Allee et al. |
| 2010/0280410 A1 * | 11/2010 | Moos ............... A61B 10/025 604/117 |
| 2011/0082425 A1 * | 4/2011 | Wuestemann ....... A61B 10/025 604/151 |
| 2011/0112436 A1 | 5/2011 | Jones et al. |
| 2012/0035501 A1 | 2/2012 | Landrigan et al. |
| 2012/0116247 A1 * | 5/2012 | Wawrzyniak ........ A61B 10/025 600/567 |
| 2012/0129676 A1 | 5/2012 | Duffy et al. |
| 2012/0136277 A1 * | 5/2012 | Landrigan ............ A61B 10/025 600/566 |
| 2013/0131545 A1 | 5/2013 | Azimpoor et al. |
| 2013/0150752 A1 * | 6/2013 | Swann ................... A61M 1/67 600/567 |
| 2014/0081318 A1 | 3/2014 | Houser et al. |
| 2015/0289858 A1 | 10/2015 | McGillicuddy et al. |
| 2016/0106462 A1 | 4/2016 | Mcgillicuddy |
| 2016/0331878 A1 | 11/2016 | McGillicuddy et al. |
| 2018/0085144 A1 | 3/2018 | McGillicuddy |
| 2019/0314004 A1 | 10/2019 | McGillicuddy et al. |
| 2020/0129680 A1 | 4/2020 | McGillicuddy et al. |
| 2020/0305930 A1 | 10/2020 | McGillicuddy |
| 2021/0038201 A1 | 2/2021 | McGillicuddy |
| 2021/0315553 A1 | 10/2021 | McGillicuddy |

FOREIGN PATENT DOCUMENTS

| | | |
|---|---|---|
| WO | WO 2010/138895 A3 | 12/2010 |
| WO | WO 2012/047984 A1 | 4/2012 |
| WO | WO 2013/096419 A1 | 6/2013 |
| WO | WO 2014/070804 A1 | 5/2014 |
| WO | WO 2015/109100 A1 | 7/2015 |

OTHER PUBLICATIONS

Non-Final Office Action for U.S. Appl. No. 17/080,999, entitled "Bone Marrow Aspiration Device and Method," dated Dec. 28, 2020.

Notice of Allowance, U.S. Appl. No. 14/885,821 entitled "Bone Marrow Aspiration Device and Method," dated Jan. 6, 2021.

Notice of Allowability & Interview Summary, U.S. Appl. No. 14/885,821 entitled "Bone Marrow Aspiration Device and Method," dated Jan. 22, 2021.

Bhootra, B.L. "1. Fatality Following a Sternal Bone Marrow Aspiration Procedure," Medicine, Science and the Law. 2004;44(2): 170-172. doi:10.1258/rsmmsl.44.2.170, 2004.

Islam, A., "New sternal puncture needle," J. Clin. Pathol, 44, pp. 690-691, 1991.

Malempati et al., "Bone marrow aspiration and biopsy," N. Engl J. Med. 36(15), NEJM.org, 2009.

U.S. Non-Final Office Action for U.S. Appl. No. 14/885,821, dated Aug. 6, 2020 entitled "Bone Marrow Aspiration Device And Method."

Interview Summary, U.S. Appl. No. 14/885,821, entitled "Bone Marrow Aspiration Device And Method," dated Oct. 14, 2020.

Al-Ibraheemi et al., "Comparison between 1-needle technique versus 2-needle technique for bone marrow aspiration and biopsy procedures," Arch Pathol Lab Med., 137(7): 974-8, Jul. 2013.

Definition of offset (Dictionary.com on Jun. 4, 2018).

Final Office Action, U.S. Appl. No. 14/885,821, entitled "Bone Marrow Aspiration Device And Method," dated Jun. 14, 2018.

Final Office Action, U.S. Appl. No. 14/885,821, entitled "Bone Marrow Aspiration Device And Method," dated Jan. 8, 2020.

Harrell. D.V., et al., "Novel Technology to Increase Concentrations of Stem and Progenitor Cells in Marrow Aspiration," downloaded from www.marrowcellutions.com on Oct. 7, 2015 (8 pages).

(56) References Cited

OTHER PUBLICATIONS

Hemigou et al., "Percutaneous Autologous Bone-Marrow Grafting for Nonunions. Surgical Technique," Tire Journal of Bone and Joint Surgery, Inc., vol. 88-A1 Supplement 1, Part 2. Sep. 2006 (7 pages).
International Preliminary Report on Patentability and Written Opinion, PCT/US2013/067358, "Apparatus And Methods For Aspirating Tissue," dated May 5, 2015.
International Preliminary Report on Patentability, PCT/US2015/011614, titled: "Bone Marrow Harvesting Needle Improvements," dated Jul. 19, 2016.
International Search Report and Written Opinion, PCT/US2013/067358, "Apparatus And Methods For Aspirating Tissue," dated Feb. 21, 2014.
International Search Report and Written Opinion, PCT/US2015/011614, "Bone Marrow Harvesting Needle Improvements," dated Apr. 20, 2015.
Interview Summary, U.S. Appl. No. 14/885,821, entitled "Bone Marrow Aspiration Device And Method," dated Oct. 9, 2019.
Islam, A., "Bone marrow aspiration before bone marrow core biopsy using the same bone marrow biopsy needle: a good or bad practice?," J Clin Pathol., 60(2): 212-215, Feb. 2007.
Muschler et al., "Aspiration to Obtain Osteoblast Progenitor Cells from Human Bone Marrow: The Influence of Aspiration Volume," The Journal of Bone and Joint Surgery, Inc., vol. 79-A, No. 11, Nov. 1997 (12 pages).
Non-Final Office Action for U.S. Appl. No. 14/439.022, "Apparatus And Methods For Aspirating Tissue," dated May 2, 2018, 21 pages.
Non-Final Office Action for U.S. Appl. No. 15/110,520, dated Dec. 17, 2018.
Non-Final Office Action for U.S. Appl. No. 15/721,123 dated Mar. 29, 2019.
Non-Final Office Action, U.S. Appl. No. 14/885,821. entitled "Bone Marrow Aspiration Device And Method," dated Sep. 11, 2017.
Non-Final Office Action, U.S. Appl. No. 14/885,821, entitled "Bone Marrow Aspiration Device And Method," dated Apr. 5, 2019.
Notice of Allowance and Fees Due, U.S. Appl. No. 15/110,520, entitled "Bone Marrow Harvesting Needle Improvements," dated Oct. 1, 2019.
Notice of Allowance and Fees Due, U.S. Appl. No. 15/721,123, entitled "Bone Marrow Access Device," dated Oct. 4, 2019.
Notice of Allowance, U.S. Appl. No. 14/439,022, entitled, "Apparatus And Methods For Aspirating Tissue," dated Nov. 2, 2018.
Notification of Transmittal of the International Search Report and the Written Opinion of the International Searching Authority, or the Declaration, "Apparatus And Methods For Aspirating And Separating Components Of Different Densities From A Physiological Fluid Containing Cells", dated Aug. 18, 2011.
Office Action for U.S. Appl. No. 14/439,022 dated Sep. 5, 2017, entitled "Apparatus And Methods For Aspirating Tissue," 27 pages.
Office Action for U.S. Appl. No. 15/110,520, entitled "Bone Marrow Harvesting Needle Improvements," dated Apr. 17, 2019.
Ranfac—Endocellutions, "Legacy Needles are designed to pull a Small Aspirate From a Single Location," downloaded from www.marrowcellutions.com on Oct. 7, 2015 (1 page).
Ranfac—Endocellutions, "Marrow Cellution™—Bone Marrow Harvesting Systems," downloaded from www.marrowcellutions.com on Oct. 7, 2015 (2 pages).
Ranfac—Endocellutions, Presentation, "Marrow Cellution," downloaded from www.marrowcellutions.com on Oct. 7, 2015 (12 pages).
Ranfac, Fact Sheet, "Marrow Cellution—Bone Marrow Aspiration and Stem Cell Harvesting Systems," downloaded from www.marrowcellutions.com on Dec. 23, 2015 (2 pages).
Restriction Requirement, Application No. 14/885.821, entitled "Bone Marrow Aspiration Device And Method," dated Mar. 21, 2017.
Scarpone, M. A. et al., "Marrow Cellution Bone Marrow Aspiration System and Related Concentrations of Stem and Progenitor Cells," downloaded from www.marrowcellutions.com on Dec. 23, 2015 (6 pages).
"Snarecoil™ Biopsy Needles—Technology that reduces the TIME and TRAUMA of Bone Marrow Biopsies," retrieved from www.ranfac.com/pdf/bonemarrow.pdf on Mar. 15, 2010, (4 pages).

\* cited by examiner

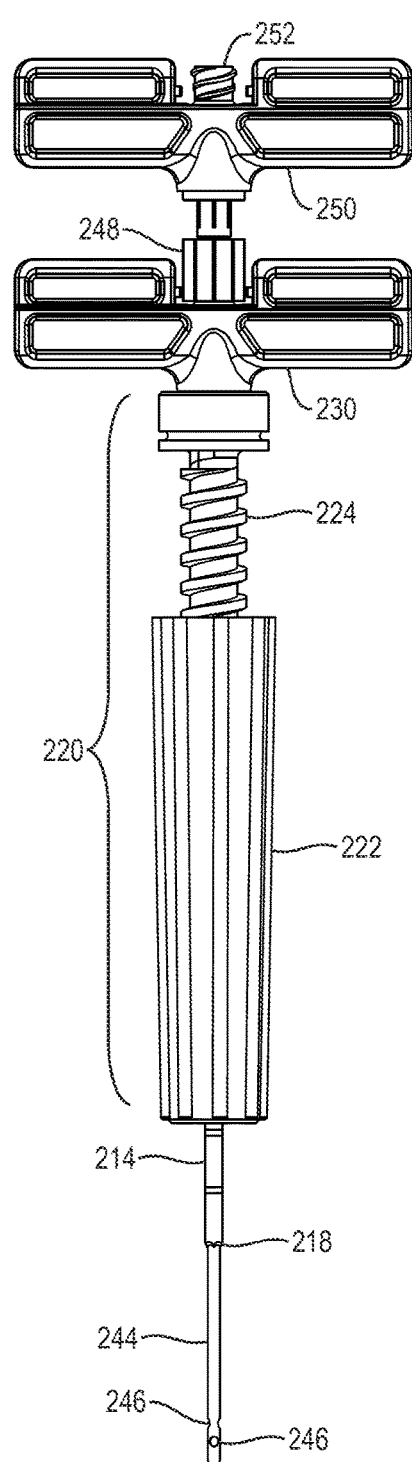
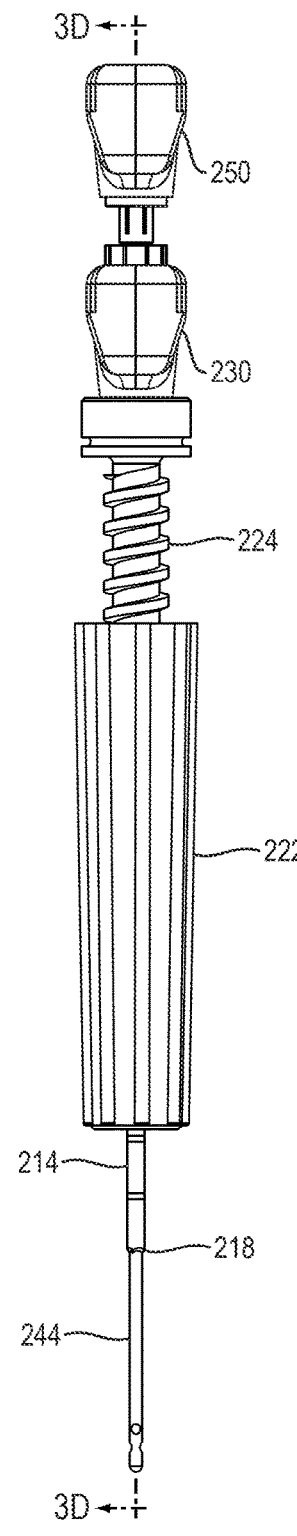
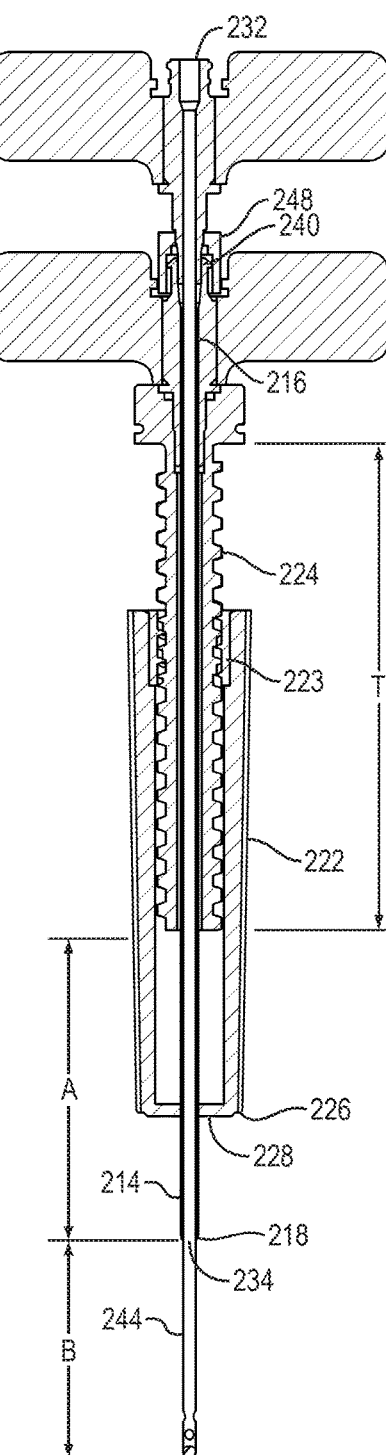
FIG. 3B
FIG. 3C
FIG. 3D

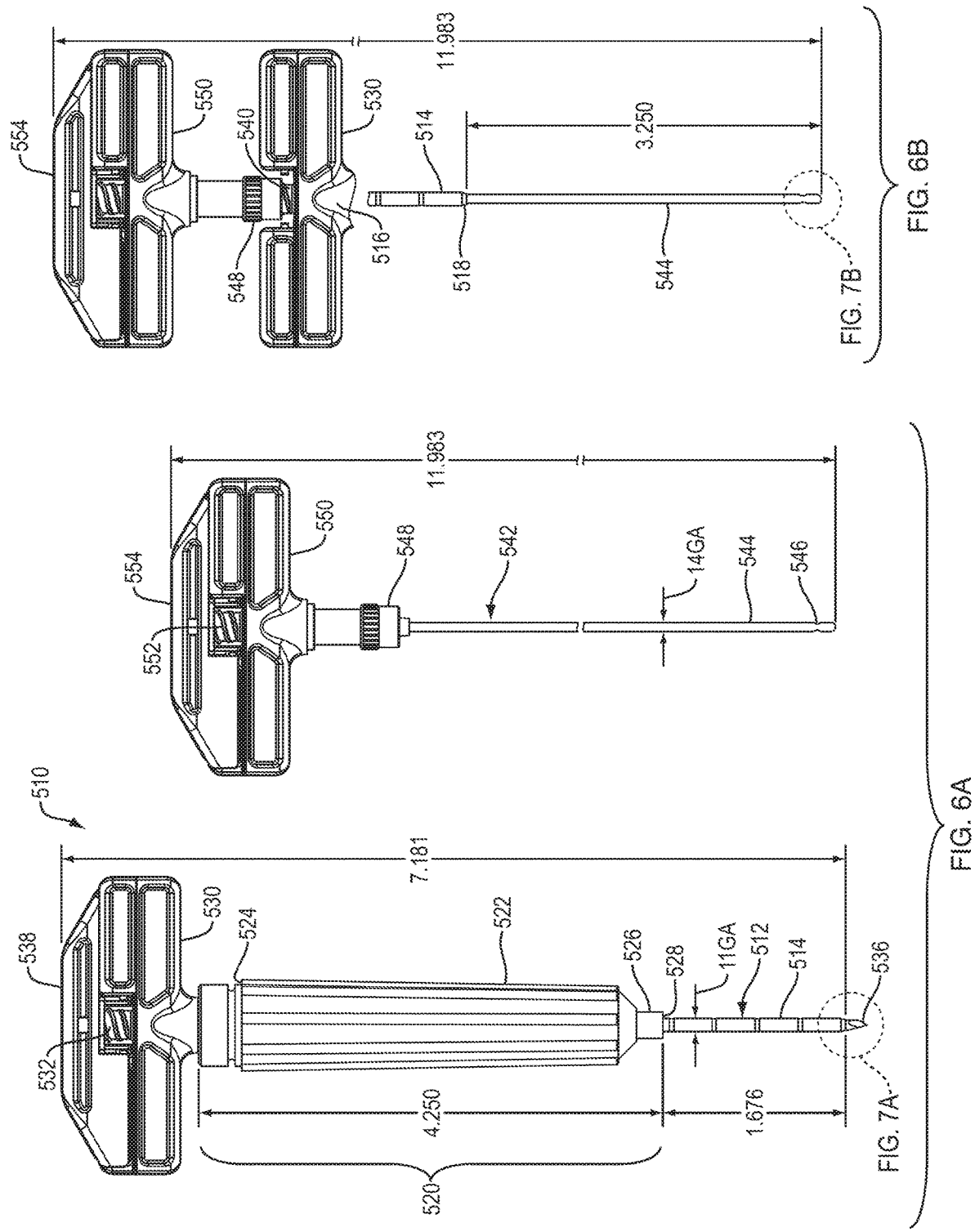

BONE MARROW ASPIRATION DEVICE AND METHOD

RELATED APPLICATIONS

This application is a divisional of U.S. application Ser. No. 14/885,821, filed Oct. 16, 2015, which claims the benefit of U.S. Provisional Application No. 62/174,849, filed on Jun. 12, 2015, and U.S. Provisional Application No. 62/065,409, filed on Oct. 17, 2014.

The entire teachings of the above applications are incorporated herein by reference.

BACKGROUND OF THE INVENTION

Bone is made up of a hard outer core, known as cortical bone or cortical plate, and a soft spongy interior known as cancellous bone or trabecular bone, which includes a marrow filling in the porous space within the spongy bone (commonly referred to as bone marrow). The cortical plate is very hard and provides the rigid structure to the skeleton, which allows the skeleton to bear weight. Bone marrow is rich in capillary beds.

A traditional bone marrow aspiration needle is commonly used to access marrow from the hip or iliac bone. The traditional aspiration needle includes an aspiration cannula (also referred to as a cannulated trocar) and a removable stylet that extends through the cannula and has a sharp tip. Once the needle is through the cortical plate, the cannula only has access to whatever marrow is directly ahead of the cannula tip, but cannot bend or access marrow to the sides of the cannula. Because the traditional needle is stiff, the needle can become stuck in the bone if inserted too deep. There is a risk that the needle breaks when the clinician attempts to forcefully remove the stuck needle. Thus, clinicians often need to perform multiple punctures using a shorted needle in order to gain larger volumes of aspirate from a more diverse cross section of the marrow space. Multiple punctures incur trauma which can interfere with the sample collection. For example, increased blood flow to the area can dilute or contaminate the aspirate, thus reducing the quality of the aspirated volume. Since the hip bone is long and thin, once the traditional aspiration needle has penetrated cortical bone, the sharp and stiff instrument has the potential to penetrate through the other side of the cortical bone, resulting in significant trauma. Consequently, it is important for the surgeon to have a proper angle and skilled technique to ensure a safe aspiration.

Therefore, a need exists for a bone marrow aspiration device that can reduce or minimize the aforementioned problems.

SUMMARY OF INVENTION

A bone marrow aspiration device includes an introducer assembly and an aspiration assembly to couple to the introducer assembly. The introducer assembly includes an introducer cannula having a proximal end and a distal end. The introducer cannula defines a lumen between the distal and proximal ends, and the distal end is configured to penetrate bone of a patient. The aspiration assembly includes an aspiration cannula that is receivable in the lumen of the introducer cannula and that extends beyond the distal end of the introducer cannula. The aspiration cannula includes a port to aspirate bone marrow, the port being distal to the distal end of the introducer cannula. The aspiration device further includes a mechanism at the introducer assembly to move the introducer cannula and the aspiration cannula in tandem relative to a distal end of the mechanism when the aspiration cannula is positioned within bone.

The mechanism can include a screw assembly that includes a threaded jacket and a lead screw receivable in the threaded jacket. At least a portion of the introducer cannula can extend through the lead screw, e.g., through a central lumen defined by the lead screw.

A length of the introducer cannula that extends from a distal end of the threaded jacket and, for example, into bone can be adjusted by advancing the lead screw into the threaded jacket, e.g., by rotating the lead screw in a first direction, or reversing the lead screw out of the threaded jacket, e.g., by rotating the lead screw in a second direction, opposite to the first direction.

The mechanism can be configured to move the introducer cannula and aspiration cannula proximally with leverage on the patient. The threaded jacket of the mechanism can define a surface to contact the patient to provide the leverage.

The screw assembly can be configured to provide a length of travel of the lead screw relative to the threaded jacket, the length of travel being between about 1.5 inches and about 5 inches. Preferable, the length of travel is between about 2 inches and about 4 inches.

An exposed length (also referred to as maximum exposed length) can include the length of the introducer cannula that extends from the distal end of the threaded jacket when the screw mechanism is fully retracted. The exposed length can include the length of the aspiration cannula that extends beyond the distal end of the introducer cannula. The exposed length can be between about 0.75 inches and about 8.5 inches. Expressed as a percentage of the length of travel, the exposed length can be, for example, between about 50% and about 200% of the length of travel. Preferably, the exposed length is between about 100% and about 150%, more preferably between about 110% and about 133% of the length of travel. In a particular example, the length of travel is about 3.25 inches and the exposed length (of introducer cannula and aspiration cannula) is about 3.5 inches, or about 108% of the length of travel.

The aspiration cannula can form a channel for aspirating bone marrow, the channel communicating with the distal port of aspiration cannula.

The aspiration assembly can include a connector, e.g., a Luer connector or other suitable connector, to couple to the introducer assembly in an air-tight manner, e.g., to form a seal to seal against air flow through the introducer cannula. The sealed coupling mechanically links the assemblies so that the cannulae can be moved in tandem and also prevents air from leaking into the marrow space through the aspiration device and being aspirated through the aspiration cannula.

A method of aspirating bone marrow includes positioning an introducer cannula of an introducer assembly in bone of a patient. With a mechanism at the introducer assembly, the introducer cannula is moved within the bone with leverage on the patient. Bone marrow is aspirated through a lumen of the introducer cannula.

Bone marrow can be aspirated while the introducer cannula is moved with the mechanism.

An aspiration cannula may be inserted through the lumen of the introducer cannula, and the bone marrow can be aspirated with the aspiration cannula. The aspiration cannula can extend beyond a distal end of the introducer cannula. An air-tight seal can be formed between the aspiration cannula and the introducer assembly, to seal against air flowing through the introducer cannula. The introducer assembly and the aspiration cannula can be coupled, for example, with a connector. Using the mechanism, the coupled cannulae can be moved together, e.g., in tandem, and relative to a portion of the mechanism.

Moving the introducer cannula with the mechanism can include moving the introducer cannula and the aspiration cannula in tandem relative to the threaded jacket of the mechanism. When moved by the mechanism, the introducer cannula and the aspiration cannula can move without relative rotation to each other.

The method can include contacting the patient with a surface of the threaded jacket to provide the leverage, and can further include adjusting a length of the introducer cannula that extends from a distal end of the threaded jacket by advancing the lead screw into the threaded jacket or reversing the lead screw out of the threaded jacket.

In an embodiment, a method of aspirating bone marrow includes inserting an aspiration cannula through an introducer cannula of an introducer assembly, the introducer cannula positioned in bone of a patient and extending beyond a distal end of the introducer cannula. The method further includes aspirating bone marrow through a port in the aspiration cannula, the port being distal to the distal end of the introducer cannula, and, with a mechanism at the introducer assembly, moving the introducer cannula and the aspiration cannula in tandem within the bone with leverage on the patient.

The mechanism, e.g., the screw assembly, can act as an adjustable guide for the introducer cannula and, when present, the aspiration cannula, to advance the cannulae in tandem into bone space (move the cannulae distally) or withdraw the cannulae in tandem from the bone space (move the cannulae proximally). Material can be aspirated or otherwise extracted from different depths within the bone space, the depth controlled by the adjustable guide.

Embodiments of the present invention have many advantages. For example, the second needle (aspiration needle, aspiration assembly) is secured to the first needle (introducer needle, introducer assembly) in an air-tight manner using a connector. In particular example, the connector includes a hollow guide through which the aspiration cannula extends, the guide being attached to the handle of the aspiration assembly. The guide is inside a threaded tube that is configured to mate to the threaded mechanism on the handle of the introducer assembly. The threaded tube can be rotatable relative to the guide and the handle of the aspiration assembly. This system of coupling the two needles prevents any air from leaking between the introducer cannula and the aspiration cannula during the aspiration process. When putting a second needle through a first needle into bone, and aspirating through the second needle, the connection between the two needles should prevent air flow between the two needles in response to the negative pressure applied to the second needle, e.g., vacuum pressure created by a syringe, to avoid the risk of air flowing into the bone and being aspirated.

The screw mechanism provides a mechanical advantage that, alone or in combination with leverage on the patient provided when pushing the distal end of the screw mechanism into the patient, can create sufficient force to retrieve a cannula lodged in the bone space. Typically, force is required to advance the second, longer needle into the marrow space, which can result in the needle becoming lodged in the marrow space. Often, a mallet is used to advance the needle. The screw mechanism can provide the force to retrieve a needle that has been advanced forcefully into bone.

Aspiration devices and method that employ a screw mechanism according to embodiments of the present invention provide a further, related advantage. The two needles, once coupled, travel in tandem during retrieval from the bone, such that the second, longer needle is not pulled over the leading edge of the first needle. When pulling a second, longer aspiration needle through a first, introducer needle, the second needle can skive on the leading edge of the first needle, which is a problem in other approaches for bone marrow aspiration. While the second, aspiration needle can be made of a material, such as steel, to avoid skiving along the leading edge of the first, introducer needle, having both needles move in tandem, as in the present approach, avoids the problem of skiving altogether.

Another advantage is that force created by the linear plane of the screw mechanism, which can retrieve a needle lodged in bone, also enables the needle, or needles moving in tandem, to be precisely re-positioned as the needle(s) is retrieved from the marrow space. For example, the screw mechanism can act as a depth guide to control the precise depth as the aspiration needle is pulled out of the marrow space. In order to optimize stem cell counts in the extracted bone marrow, it is beneficial to reposition the aspiration needle precisely as the needle is retrieved from the medullary space. Each new location represents a new location for aspiration.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 3B-3D are front, side and sectional views, respectively, of the aspiration device of FIG. 3A illustrating the aspiration cannula inserted through the introducer cannula.

FIG. 6A illustrates another example aspiration device including an introducer assembly with an introducer cannula and a sharp stylet, a guide mechanism and an aspiration assembly with an aspiration cannula and a blunt stylet.

FIG. 6B illustrates the aspiration assembly of FIG. 6A coupled to the introducer assembly after the sharp stylet has been removed.

DETAILED DESCRIPTION OF THE INVENTION

Figure 1A:
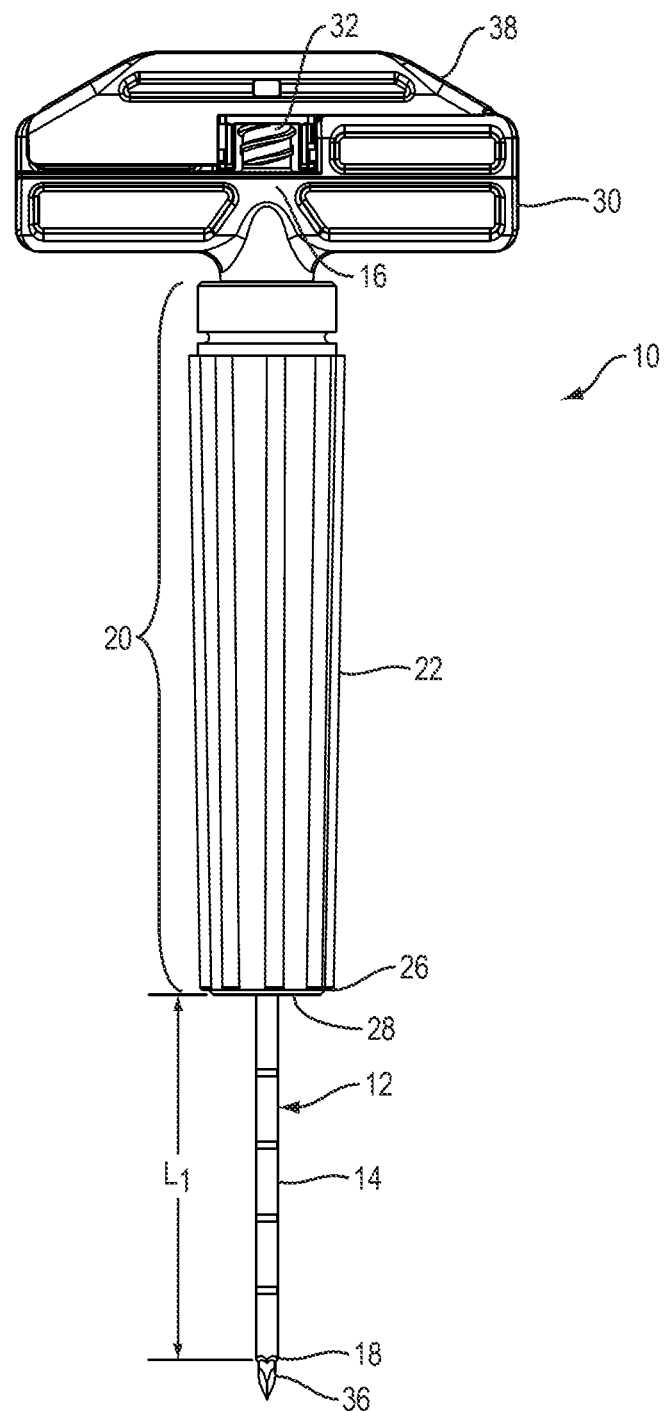
FIG. 1A illustrates an example aspiration device including an introducer cannula, a sharp stylet and a guide mechanism.

A description of example embodiments of the invention follows below and in the appended pages.

Bone marrow aspiration devices including an introducer cannula and an aspiration cannula are described in International Application No. PCT/US2010/036696, filed on May 28, 2010 and published on Dec. 2, 2010 as WO2010/138895 A2, and International Application No. PCT/US2013/067358, filed on Oct. 29, 2013 and published on May 8, 2014 as WO2014/070804 A1, the teachings of which are incorporated herein by reference in their entireties.

A method of aspirating tissue according to the present approach can include positioning a needle in tissue, e.g., bone, and pulling back the needle from the tissue through a mechanism, e.g., a screw, a step turn, or stepper motor. Aspiration can occur before, during, or after the needle is moved. For example, the cannula can be moved mechanically forward or backward (distally or proximally) while aspirating. Movement of the cannula can be incremental, e.g., a step, and in a controlled fashion, e.g., through a screw mechanism. For example, a screw mechanism may be configured to move the cannula forward or backward by 1 cm for every 360 degree turn of the screw. The screw may be coupled to a handle attached to the cannula for manual operation. The screw mechanism can include a jacket that is threaded and through which the screw travels. The threaded jacket can be large enough, i.e., be of sufficient axial length, to be easily grasped by one hand while the operator uses the other hand to turn the screw. The jacket can also provide leverage when the cannula is withdrawn from the bone space using the screw mechanism. Aspiration can occur after an incremental movement of the cannula into or out of the bone through the mechanism. For example, it may be advantageous to aspirate bone marrow as the cannula is advanced into the bone space. The cannula can comprise an introducer cannula and an aspiration cannula.

In some embodiments, aspiration is done through a relatively big hole (port) at the distal end of a cannula that is positioned in the bone space. For example, the diameter of the hole can be as big as the inner diameter of the cannula, e.g., the inner diameter of the introducer cannula. Aspiration may be through one or more holes that are smaller, e.g., side holes (ports) in the cannula. For example, the diameter of a side hole can be smaller than the inner diameter of the introducer cannula. An aspiration cannula may be inserted through an introducer cannula. A relatively big hole at the distal end of the introducer cannula can be closed off by the aspiration cannula, which may have a closed distal end. Side holes may be positioned along the length of the aspiration cannula, e.g., near the distal end of the aspiration cannula, for aspirating bone marrow. Advantageously, an aspiration cannula having side ports and a closed distal end can preferentially draw marrow from the side ports, while avoiding peripheral blood which can fill the open channel created in the marrow space by the retracting cannula during the aspiration process.

Aspiration devices of the present invention may use cannula sizes in the range of 6 Gauge to 31 Gauge. A cannula may have an outer diameter in the range of 0.25 inches to 0.01 inches.

In some embodiments, the aspiration cannula is 14 Gauge or bigger. The introducer cannula can be 11 Gauge or bigger.

Configurations of the aspiration device that may be adjusted for a particular application include the length of the cannula (e.g., the length of introducer cannula), the length of the screw and the length of travel of the screw within the jacket, and the ratio of the length of the screw to the length of the cannula. In some embodiments, the length of travel is at least half the distance of the overall length of the cannula.

An aspiration device may include a handle. Advantageously, the handle can be attached to the cannula of the device in such a way as to permit a certain amount of torque to be applied to the cannula as the cannula is moved within the bone. The handle can also be attached to the lead screw. Suitable ways of attaching the handle to the cannula, the screw or both the cannula and screw can include using an adhesive, co-molding, or using a hex fit, among others. The handle can include winged portions for ease of manual gripping and application of torque.

The jacket of the screw mechanism provides leverage when the cannula is withdrawn from bone with the screw mechanism. Once the cannula is position in the bone to a certain depth, the jacket can be screwed down against the skin of the patient. Once the jacket is against the patient, continued rotation of the screw, e.g., by rotating the handle of the cannula, pulls the cannula out of the bone. Embodiments of the invention include a jacket that is sized such that it can be held firmly with one hand while the other hand can be used to turn the handle.

In some embodiments, the aspiration assembly may be configured for use in oncology applications. In oncology, typically only a small sample volume is needed, but one may want to sample from different depths within the bone space. An oncology aspiration cannula may have a smaller diameter. The mechanism that moves the oncology aspiration cannula may be configured for long enough travel of the cannula into the bone.

FIG. 1A illustrates an example bone marrow aspiration device 10 including an introducer cannula 14, a sharp stylet 36 and a guide mechanism 20. Aspiration device 10 includes an introducer assembly 12 that includes an introducer cannula 14 having a proximal end 16 and a distal end 18. The introducer cannula 14 defines a lumen between the distal and proximal ends. The distal end 18 of the cannula 14 is configured to penetrate bone. Sharp stylet 36 can be inserted through the lumen of the cannula 14 for penetration of bone, in particular cortical bone. As shown, the sharp tip of the stylet 36 extends through distal opening 34 in the introducer cannula and beyond the distal end 18 of the introducer cannula. Advantageously, handle 38 of the stylet interlocks with handle 30 of the introducer cannula. The aspiration device 10 includes a mechanism 20 at the introducer assembly to move the introducer cannula 14 proximally or distally. As shown, the mechanism 20 is positioned distal to the handle 30 of the introducer cannula. The mechanism 20 is configured to move the introducer cannula 14 with leverage on the patient when the cannula is positioned within bone.

Figure 1B:
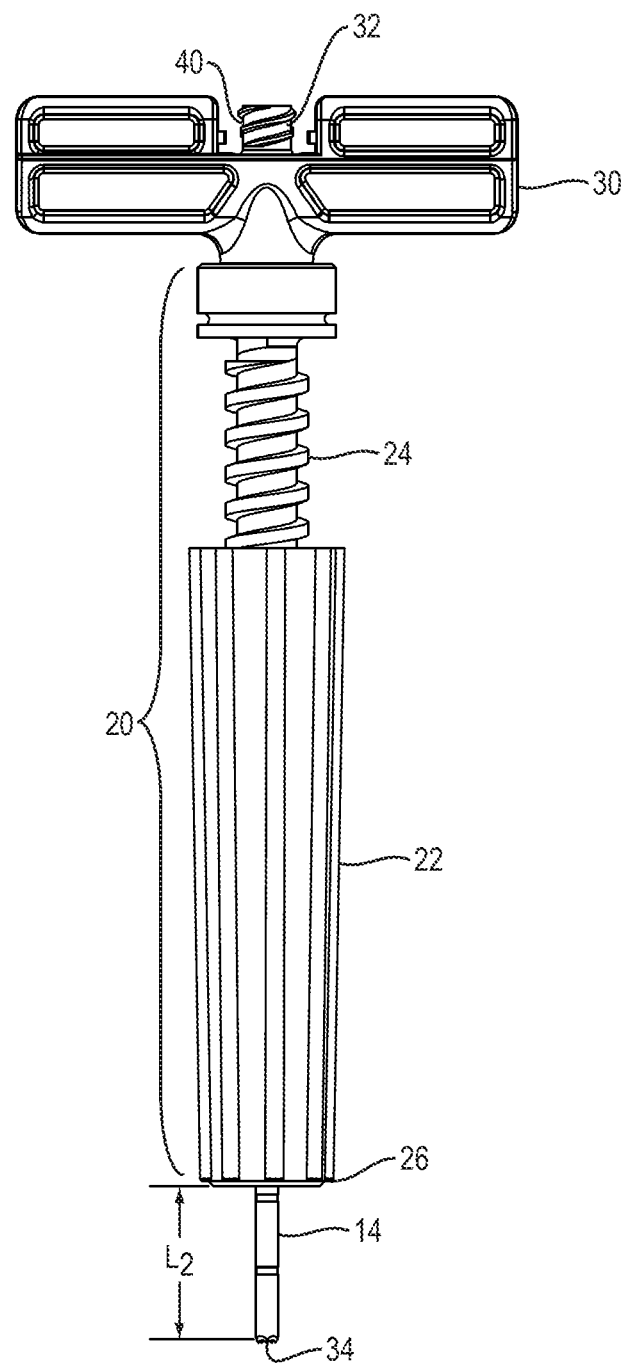
FIG. 1B illustrates the aspiration device of FIG. 1A with the style removed and with partial extension of the guide mechanism.
Figure 8:
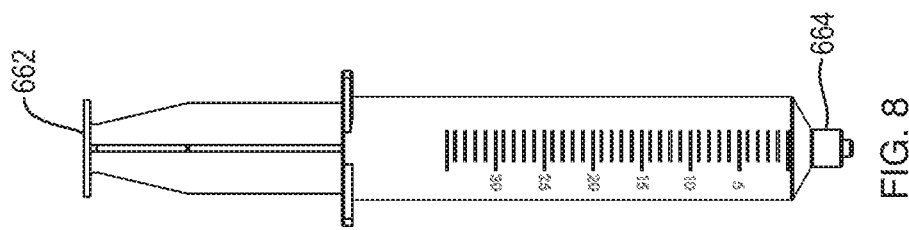
FIG. 8 is an example syringe for use with embodiments of the present invention.

As illustrated in FIGS. 1A-1B, the mechanism 20 (also referred to herein as a screw set) includes a screw assembly that includes a threaded jacket 22 and a lead screw 24 receivable in the threaded jacket. The threaded jacket includes an interior threaded portion that cooperates with an external threaded portion of the lead screw (see also FIG. 3D and associated description). A length of the introducer cannula 14 that extends from a distal end 26 of the threaded jacket and into bone can be adjusted by advancing the lead screw into the threaded jacket or reversing the lead screw out of the threaded jacket. For example, in FIG. 1A, the introducer cannula 14 extends a length $L_1$ beyond the distal end 26, while in FIG. 1B, the cannula extends a length $L_2$ from the distal end 26, $L_2$ being shorter than $L_1$. In FIG. 1B, the lead screw 24 has been reversed out of the jacket 22 and the mechanism 20 is shown in a partially extended configuration. As further described below, the distal end 26 of the threaded jacket defines a surface 28 for contacting the skin of the patient. The lead screw 24 of mechanism 20 is attached to the handle 30 of the introducer needle 12. As shown, the handle 30 includes winged portions. A port 32 is provided at the handle 30 to connect to another device. The port 32 is in fluid communication with the lumen of the introducer cannula 14 and with distal port 34. A syringe or another source of vacuum can be coupled to port 32 to aspirate material, e.g., bone marrow, through cannula 14 after the stylet 36 is removed from the introducer cannula. As shown in FIG. 1B, a connector 40, e.g., a threaded female Luer connector, is provided at the port 32 and can couple to a corresponding connector of another device. For example, connector 40 can couple to connector 664, e.g., a male Luer connector, of syringe 662 shown in FIG. 8. As will be described below with respect to FIGS. 2A-3G, the connector can also couple to a connector of an aspiration assembly.

Use of aspiration device 10 will now be described. The aspiration device 10 can be used for a variety of different purposes. As described herein, for example, the device 10 can be used to aspirate bone marrow from bone.

The embodiment illustrated in FIG. 1A-1E includes an introducer assembly 12 having single cannula 14 with a screw set 20. The screw set is used to anchor the assembly 12 against the patient so that an operator can use the screw 24 to retrieve the cannula 14 from the body in a controlled manner using the patient as leverage. The screw set 20 is used to control the depth of the cannula as it is retrieved from the body. Anchoring the outer jacket 22 of the screw set 20 against the patient and unwinding the screw 24 enables precisely repositioning of the distal opening of the cannula to a new aspiration location. The distal end 26 of the jacket 22 presses against the patient and provide the leverage to extract the cannula using this method. The screw set 20 can also be used to control how deep the cannula is advanced into the body, e.g., the bone space.

Figure 1C:
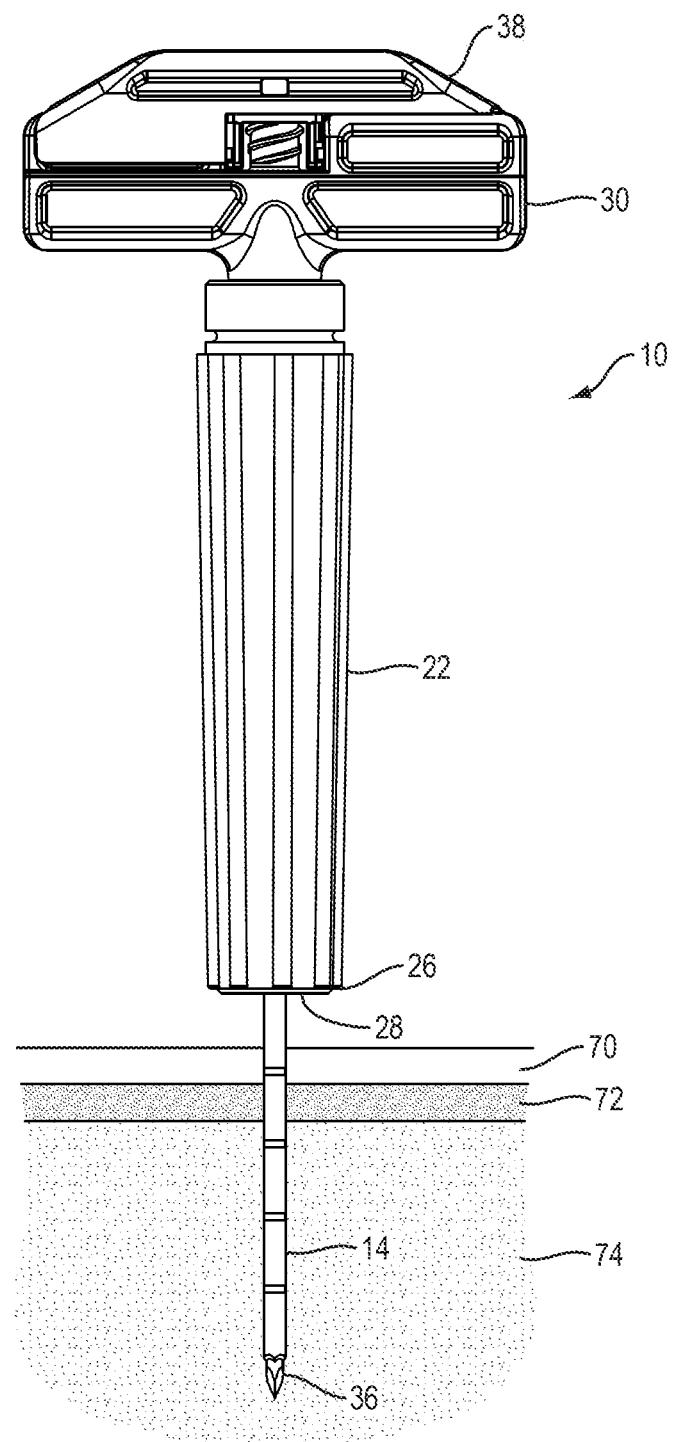
FIG. 1C illustrates insertion of the introducer cannula of the aspiration device of FIG. 1A through skin into bone.

As illustrated in FIG. 1C, the introducer cannula 14 of the aspiration device 10 with the sharp stylet 36 in place is inserted through skin 70, cortical bone 72, and into bone marrow 74. As shown in FIG. 1C, the distal end 26 of the jacket 22 has not reached the skin surface. At this point, the jacket 22 may screwed down against the patient's skin 70 so that the surface 28 is flush with the skin surface. If further penetration of the cannula 14 into bone is desired, force can be applied to the handle 38 at the proximal end of the device 10 to drive the cannula deeper into the bone.

Figure 1D:
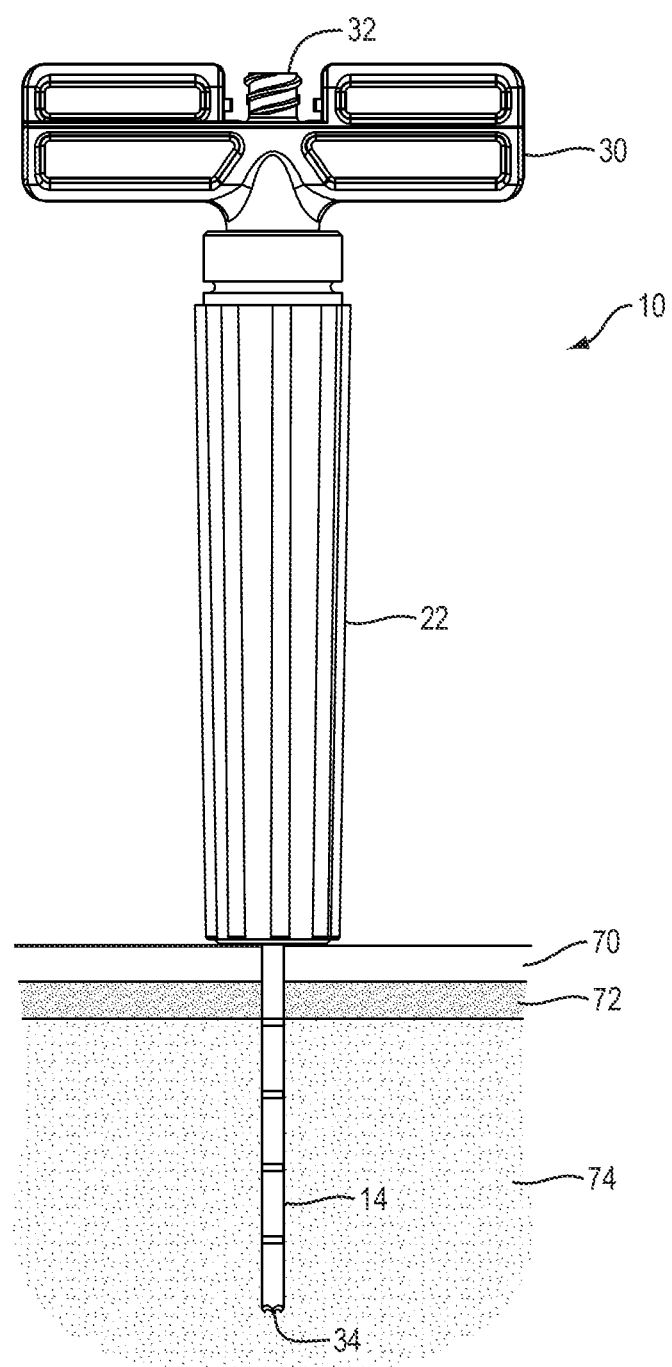
FIG. 1D illustrates the aspiration device of FIG. 1C with the cannula positioned in bone and the stylet removed.

FIG. 1D illustrates the aspiration device 10 of FIG. 1C with the cannula 14 positioned in bone and the stylet 36 removed. Once stylet is removed, a channel is created to the bone space, and a syringe (see FIG. 8) can be attached to the luer port 32 on the top hub of the device 10. Marrow can be aspirated through opening 34 at the distal end of cannula 14 and into a syringe coupled to port 32.

Figure 1E:
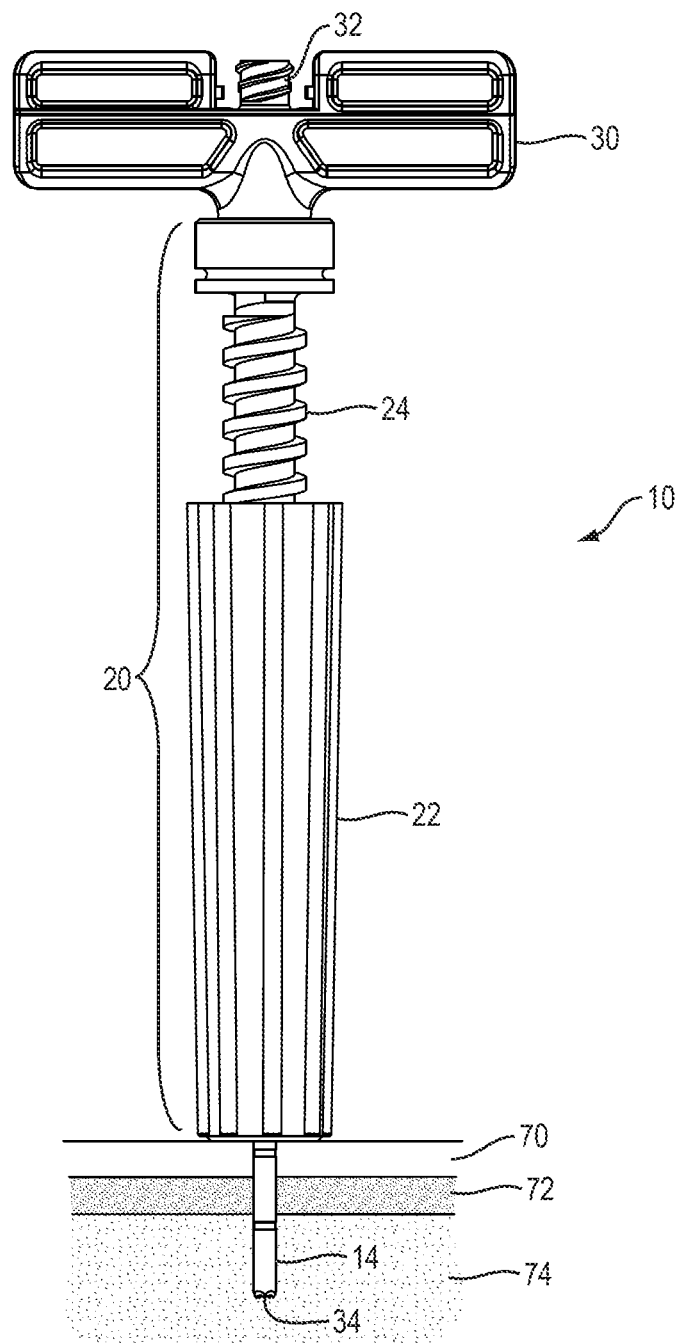
FIG. 1E illustrates the aspiration device of FIG. 1D with the cannula partially withdrawn from the bone.

FIG. 1E illustrates the aspiration device 10 of FIG. 1E with the cannula 14 partially withdrawn from the bone. The cannula 14 has moved proximally to different depth by turning the handle 30, which is attached to lead screw 24, in a counter clockwise direction. This counter clockwise movement causes the mechanism 20 to expand axially creating pressure against the patient, which allows the cannula 14 to move a precise distance out of the body. Advantageously, the lead screw 24 and the jacket 22 are configured, e.g., they have sufficient lengths relative to the length of the cannula 14, to provide sufficient length of travel to withdraw the cannula 14 in a controlled manner from the bone. As in FIG. 1D, marrow can be aspirated at the new location shown in FIG. 1E through opening 34 at the distal end of cannula 14 and into the syringe. Each new location allows for a fresh aspirate of marrow.

The following are advantageous features of an aspiration device such as device 10. The device has a full handle to create sufficient torque (for example, at least 5 ft-lbs) to unscrew and remove the cannula from the bone space after insertion. The handle of the device and its connection to the screw set 20 can withstand a certain minimum torque. Deep insertion into the bone space can result in the cannula getting lodged. When positioning the cannula and aspirating using the screw set 20, the patient provides leverage to remove the cannula as bone marrow is aspirated. As an illustrative analogy, the patient's body provides leverage similar a bottle that provides leverage to remove the cork using a corkscrew.

The length and width of the screw jacket 22 is such that the jacket can be easily grasped with a full hand even after the exposed cannula 14 has been fully inserted into the body. The travel distance of the screw 24 inside the jacket 22 is about the same as the length of the outer screw jacket. The travel distance of the screw set is such that, in a fully collapsed position (e.g., as shown in FIG. 1A), the screw set allows the exposed cannula to penetrate the bone space and then, from that position, the screw set can retract the exposed cannula from the body and into the fully extended screw set.

Example combination of dimensions that work are:

(a) Screw travel is greater than about 1.5 inches (preferably about 3 inches) and (b) Screw jacket axial length is greater than about 1.5 inches (preferably about 3.5 inches)(e.g., big enough to be easily grasped and secured in someone's hand).

(c) Distance that the cannula penetrates bone space is greater than about 1.5 inches (preferably about 3 inches)

The aspiration device 10 can come with a blunt stylet to replace the sharp stylet used to penetrate cortical bone. The blunt stylet can be used to advance further into bone space, e.g., into trabecular bone 74, and can prevent the cannula to pass through cortical bone once the bone space is traversed.

An additional bone marrow aspiration device 110 is illustrated in FIGS. 2A-2D. The aspiration device 110 is similar to the aspiration device 10 described above. Similar features are designated using like reference numbers, but increased by 100. With respect to such similar features, the above description of device 10 also applies to the device 110.

Figure 2A:
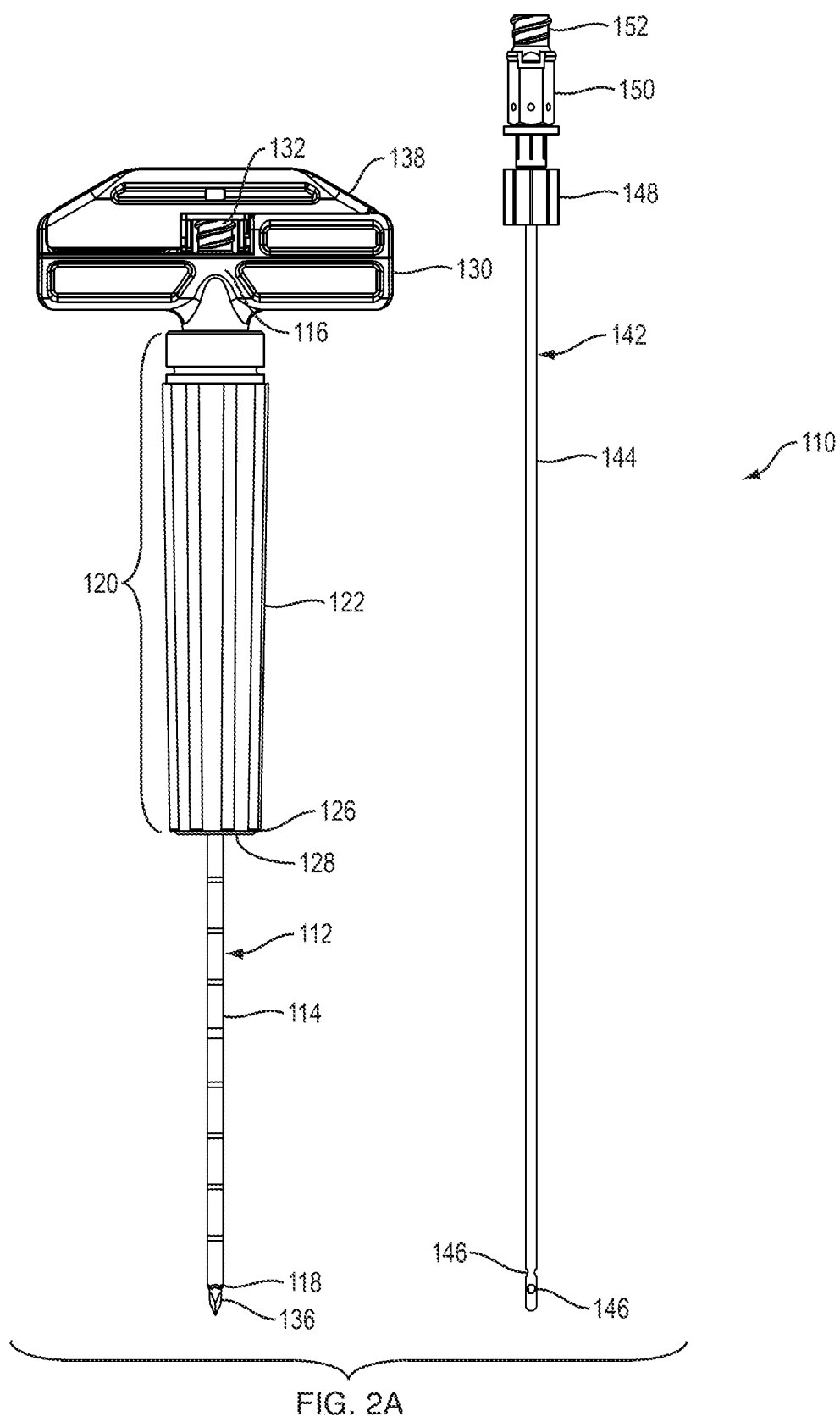
FIG. 2A illustrates another example aspiration device including an introducer cannula, a sharp stylet, a guide mechanism, and an aspiration cannula.
Figure 2B:
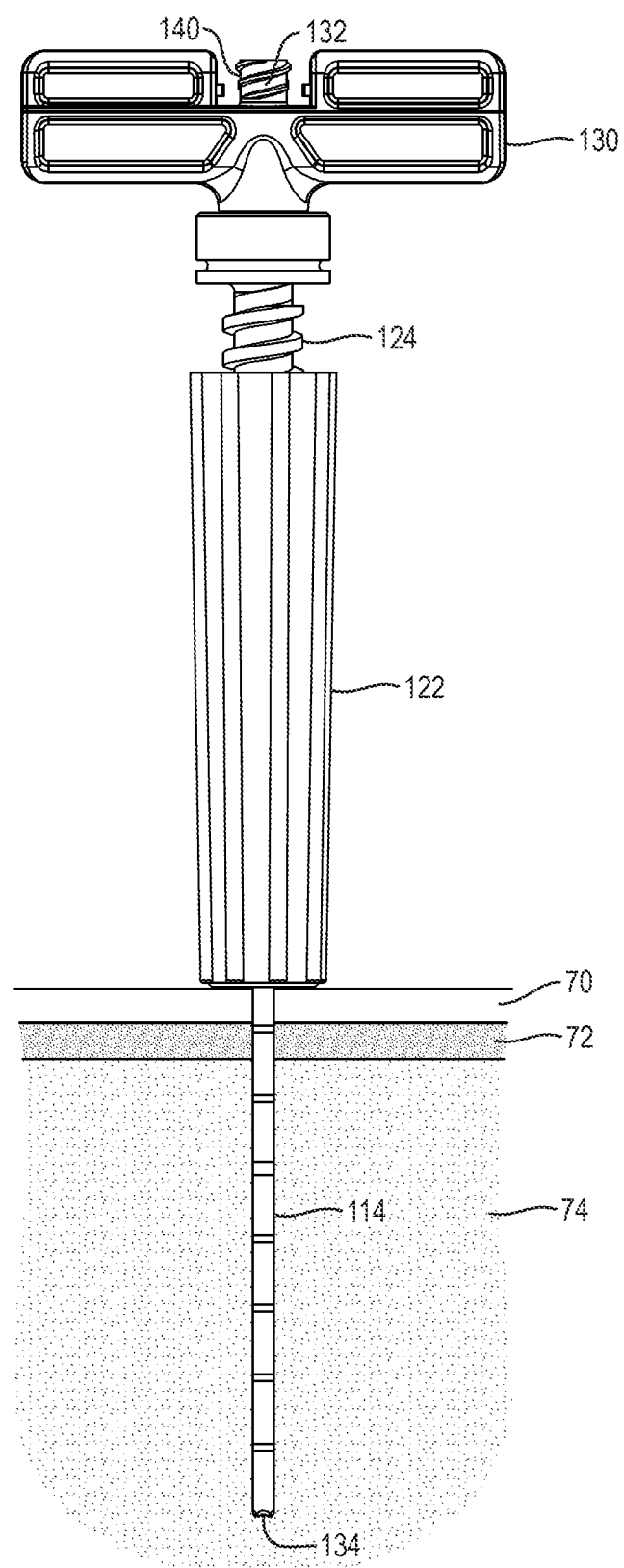
FIG. 2B illustrates the introducer cannula of FIG. 2A inserted into bone with the stylet removed.
Figure 3A:
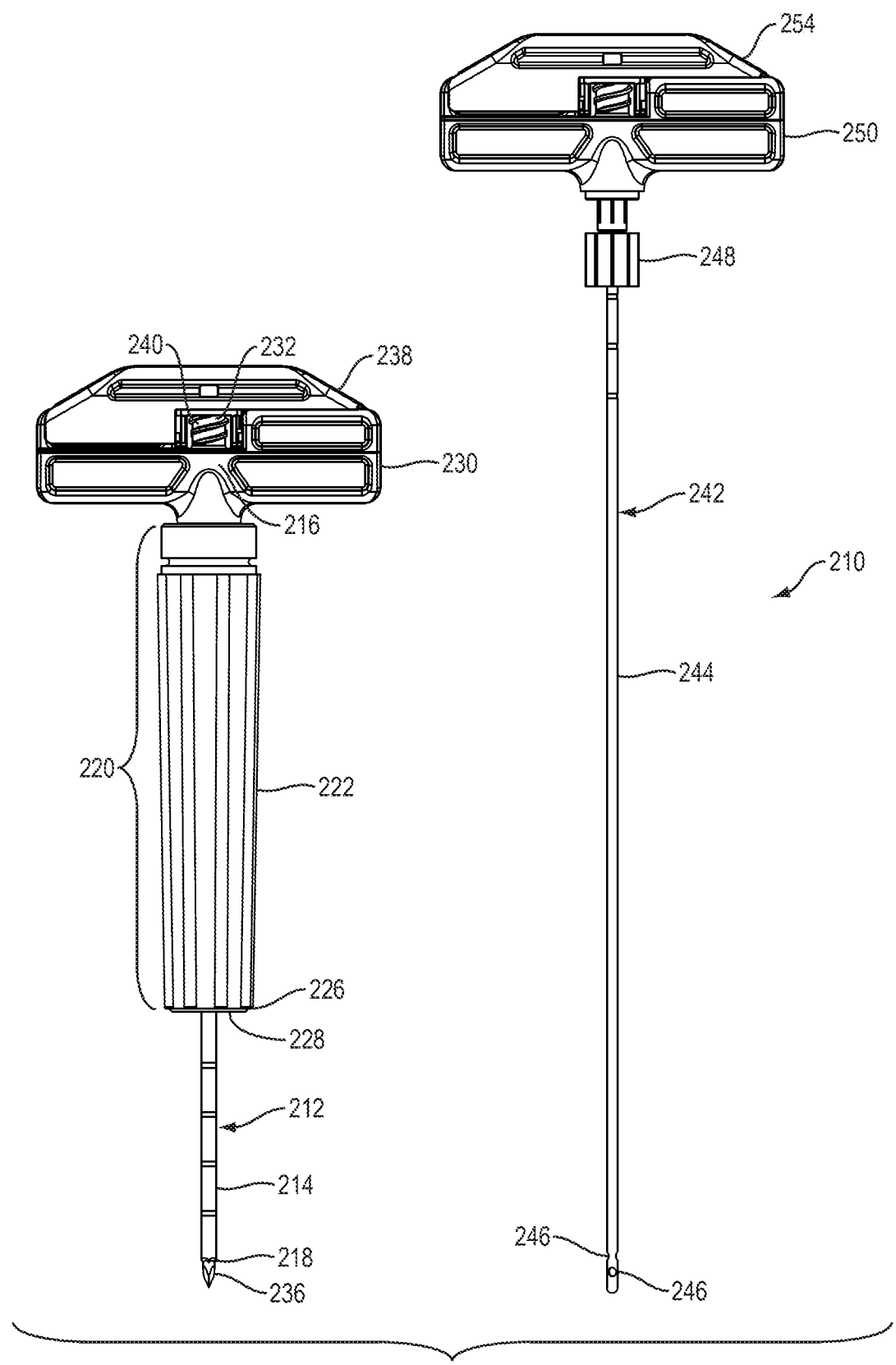
FIG. 3A illustrates another example aspiration device including an introducer cannula, a sharp stylet, a guide mechanism, and aspiration cannula including a blunt stylet.

As with aspiration device 10, the aspiration device 110, illustrated in FIGS. 2A-2B, generally includes an introducer assembly 112 with handle 130 and port 132, an introducer cannula 114 with respective proximal and distal ends 116 and 118, and a mechanism 120 that includes a threaded jacket 122 and a lead screw 124. The distal end 126 of the jacket 122 defines a surface 128 for contacting the skin of the patient. The device 110 further includes a sharp stylet 136 having a handle 138 that interlocks with handle 130. Unlike the device 10 illustrated in FIGS. 1A-1E, the device 110 includes an aspiration assembly 142 to couple to the introducer assembly 112 at port 132 through connector 140. In addition, the introducer cannula 114 can be longer than the introducer cannula 14 of device 10. Aspiration through the aspiration assembly, when inserted through introducer cannula 114, allows, for example, for aspiration from deeper inside the marrow space.

As shown in FIG. 2A, the aspiration assembly 142 includes an aspiration cannula 144 that is receivable in the lumen of the introducer cannula 114 once the sharp stylet 136 is removed. The aspiration assembly 142 includes connector 148 that is configured to cooperate with connector 140 of the introducer assembly to couple the assemblies to each other. The aspiration cannula 144 includes ports 146 to aspirate bone marrow. The ports 146 are side ports in the aspiration cannula near its distal end, which is closed and has a blunt tip. When the aspiration cannula 144 is fully inserted into the introducer cannula 114, the cannula 144 extends through opening 134 and beyond the distal end 118 of the introducer cannula such that the ports 146 are positioned distal to the distal end 118 of the introducer cannula, as for example illustrated in FIG. 2C.

The aspiration cannula defines a lumen for aspiration bone marrow. The lumen is in communication with the distal ports 146 and a port 152 at the handle 150 of the aspiration assembly. A syringe or other source of vacuum can be coupled to port 152 to aspirate material, e.g., bone marrow, through aspiration cannula 144. As shown, a connector, e.g., a threaded female Luer connector, at the port 152 can couple to a corresponding connector of a syringe or other source of vacuum.

The embodiment of FIGS. 2A-2G is an aspiration device 110 that includes a screw set 120 similar to the screw set 20 of device 10. A second, aspiration cannula 144 is inserted through the first, introducer cannula 114. The aspiration cannula 144 attaches to the Luer hub on the proximal end to the introducer assembly 112, the cannula 144 extending just beyond the distal end of the cannula 114. The aspiration cannula 144 has a blunt closed tip with two sets of side holes 146 arranged 180 degrees rotated from each other. The stylet 136 of the introducer cannula 114 protrudes from the distal end of the cannula an equal or greater distance than the aspiration cannula 144. The stylet, upon removal from the introducer cannula, leaves a path in the bone for the aspiration cannula, which, similar to the stylet, protrudes a short distance beyond the end of the introducer cannula. A stub handle 150 is sufficient for this embodiment. Typically, little or no force is needed to insert the aspiration cannula 144 because the aspiration cannula does not travel far beyond the distal end of the introducer cannula 114 and because the cannula can follow the path of the stylet 136.

In FIG. 2B, the introducer cannula 114 of device 110 is shown inserted into bone with the stylet 136 removed and the distal surface of the screw mechanism 120 secured against the patient. Once the stylet is removed, a channel is created to the bone space through which the aspiration cannula can be inserted.

Figure 2C:
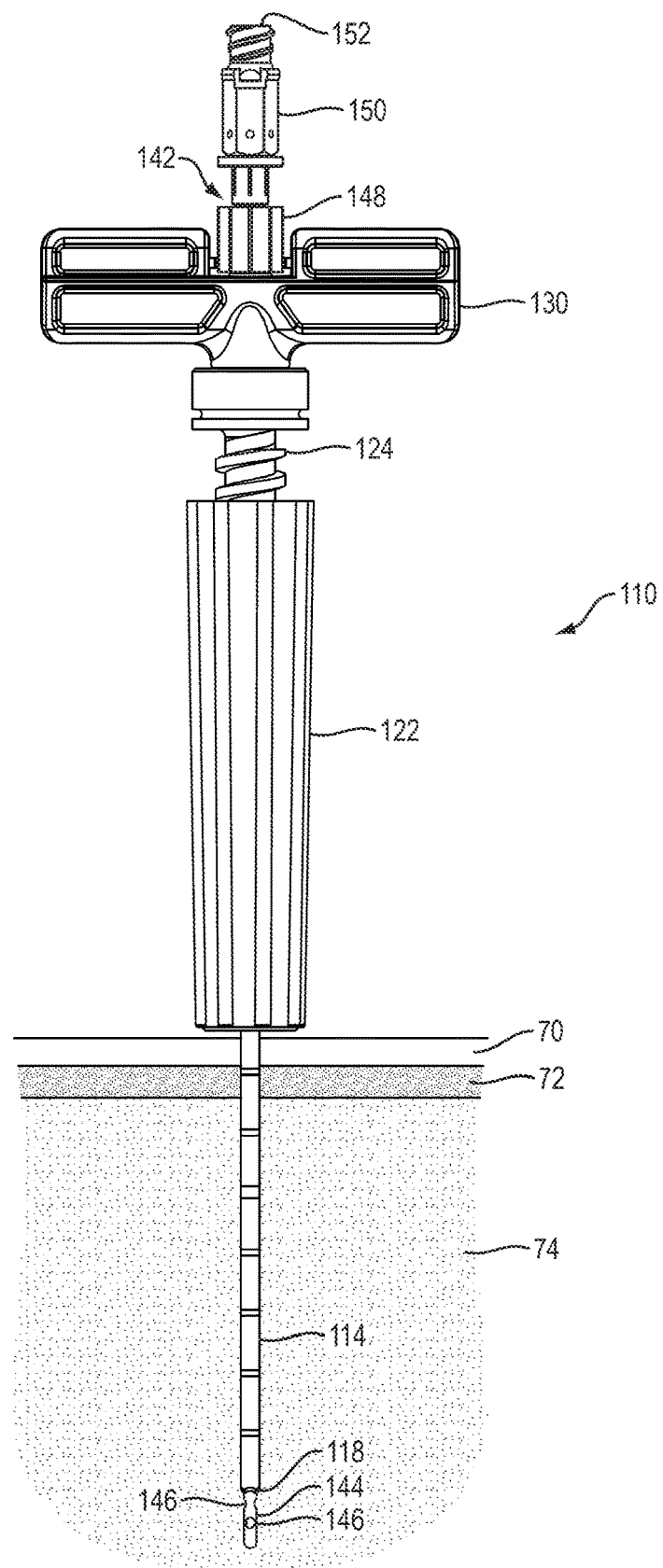
FIG. 2C illustrates the aspiration cannula of the device of FIG. 2A inserted through the introducer cannula and into bone.

FIG. 2C illustrates the aspiration cannula 144 of the device of FIG. 2A inserted through the introducer cannula 114 and into bone. The aspiration cannula 144 is secured to the introducer cannula 114 via the connector 148 creating an air tight seal as previously described. The aspiration cannula 144 travels just past the distal end of the introducer cannula 114, about the same distance the introducer stylet protrudes past the distal end of the introducer cannula prior to removal of the stylet. A syringe (see FIG. 8) can be attached to the luer port 152 on the top hub of the aspiration assembly 142. Marrow can be aspirated through the side holes 146 at the distal end of aspiration cannula 144 and into a syringe coupled to port 152.

Figure 2D:
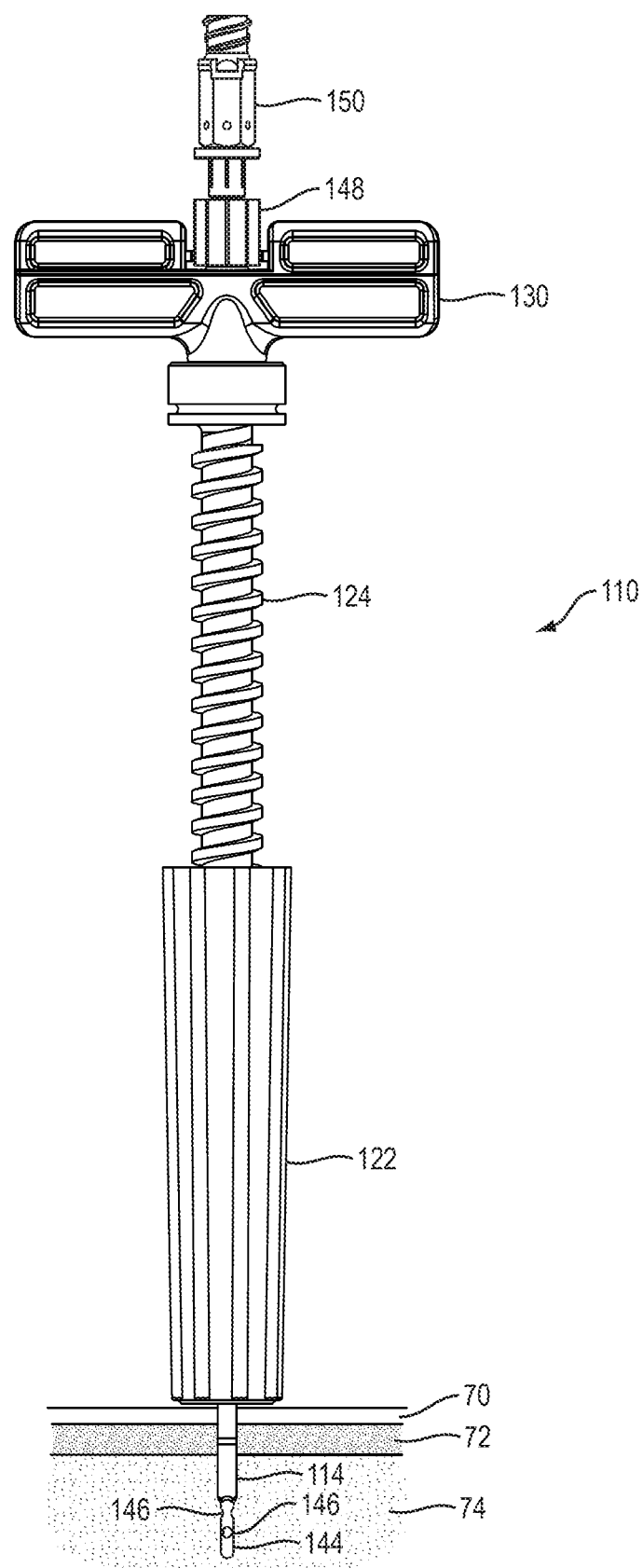
FIG. 2D illustrates the aspiration cannula and introducer cannula of FIG. 2C partially withdrawn from the bone with the guide mechanism.

In FIG. 2D, the aspiration cannula 144 and introducer cannula 114 of FIG. 2C have been partially withdrawn from the bone with the guide mechanism 120. The two cannulae 114 and 144 are retracted from the body in a controlled manner employing mechanism 120, each new depth upon retrieval creating a new spot to aspirate. The aspiration of marrow can continue through the side holes 146. The process of moving the cannulae and aspirating at a new position may be repeated until sufficient aspirate has been obtained.

An additional bone marrow aspiration device 210 is illustrated in FIGS. 3A-3G. The aspiration device 210 is similar to the aspiration device 110. Similar features are designated using like reference numbers, but increased by 100. With respect to such similar features, the above description of device 110 also applies to the device 110.

As with aspiration device 110, the aspiration device 210 generally includes an introducer assembly 212 with handle 230 and port 232, an introducer cannula 214 with proximal and distal ends 216 and 218, respectively, and a mechanism 220 that includes threaded jacket 222 and lead screw 224, as illustrated in FIGS. 3A-3D. A distal end 226 of the jacket 222 defines a surface 228 for contacting the skin of the patient. As with device 110, the device 210 further includes a sharp stylet 236 having a handle 238 that interlocks with handle 230. The device 210 also includes an aspiration assembly 242 to couple to the introducer assembly 212 at port 232 through connector 240. The aspiration assembly 242 includes an aspiration cannula 244 with side ports 246, a connector 248 configured to cooperate with connector 240 of the introducer assembly to couple the assemblies to each other, and a port 252 for connecting a syringe or other device. As with the side ports of device 110, when the aspiration cannula 244 is fully inserted into the introducer cannula 214 and extends through the distal opening 234, the side ports 246 are positioned distal to the distal end 218 of the introducer cannula, as for example illustrated in FIGS. 3B-3D.

Figure 4:
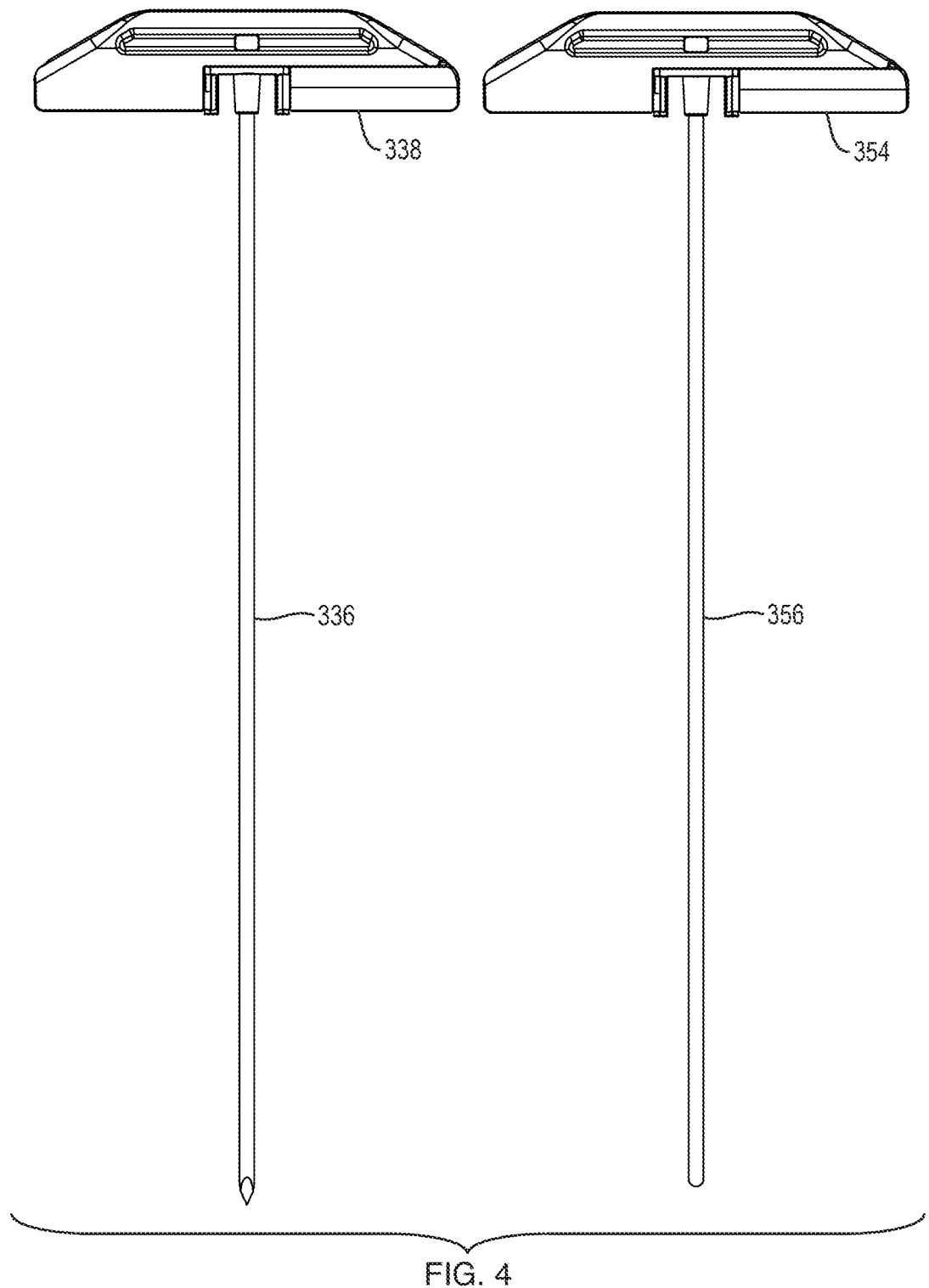
FIG. 4 illustrates a sharp stylet and a blunt stylet for use with embodiments of the present invention.

Unlike in the aspiration device 110, which is configured such that the aspiration cannula only extends a short length beyond the distal end of the introducer cannula, the aspiration device 210 is configured such that the aspiration cannula 244 extends substantially further beyond the distal end of the introducer cannula 214. To facilitate insertion of the cannula 244 into bone space beyond the distal end of the introducer cannula, aspiration device 210 is provided with a handle 250 that includes winged portions and with a blunt stylet whose handle 254 can interlock with the handle 250 of the aspiration assembly. An example blunt stylet 356 is shown in FIG. 4. The blunt stylet provides stiffness to the aspiration cannula 244, and the handles 250 and 254 enable application of axial force during the insertion of the aspiration cannula into bone.

The embodiment illustrated in FIGS. 3A-3G is similar to the embodiment illustrated in FIGS. 2A-2D in many aspects, but differs in that the aspiration cannula 244 travels a greater distance beyond the introducer cannula 214 and is provided with a full handle 250. The aspiration cannula can, for example, extend distally beyond the distal end of cannula 214 by about 1 inch to about 1.5 inches. The aspiration cannula 244 has a full handle 250, e.g., a handle with winged portions, because force is typically needed to advance the cannula 244 past the distal end of the cannula 114 and into the marrow space. The screw mechanism 220 on the introducer assembly 212 serves as a depth guide for the longer aspiration cannula 244 to which it is not attached. This is so because, once the screw set of the introducer assembly 212 is anchored against the patient, the handle 230 of the introducer assembly can be turned counter clockwise, which causes the introducer cannula 214 to rise up out of the bone and engage the aspiration cannula 244.

Figure 3E:
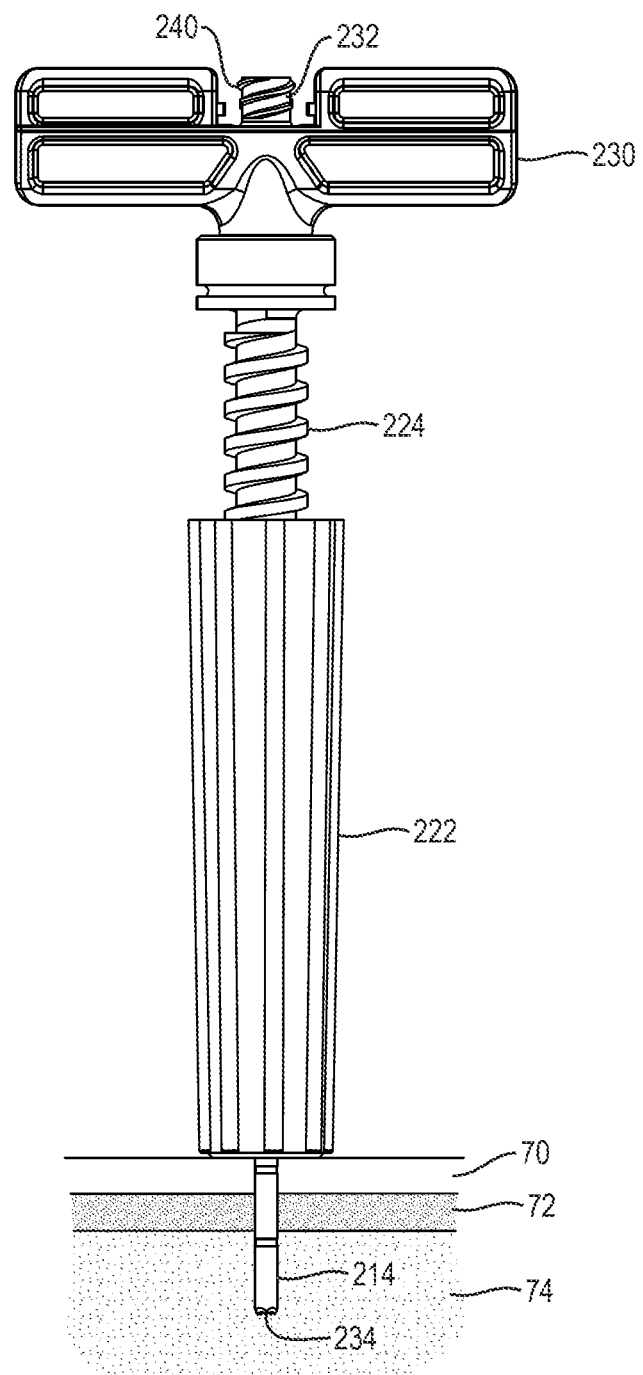
FIG. 3E illustrates the aspiration device of FIG. 3A with the introducer cannula inserted into bone and the sharp stylet removed.

FIG. 3E illustrates the introducer cannula 214 of device 210 inserted into bone (72, 74). The introducer cannula 214 is extended into the body, the jacket 222 secured to the skin 70 of patient, and the sharp stylet 236 has been removed creating a channel for the aspiration cannula.

Figure 3F:
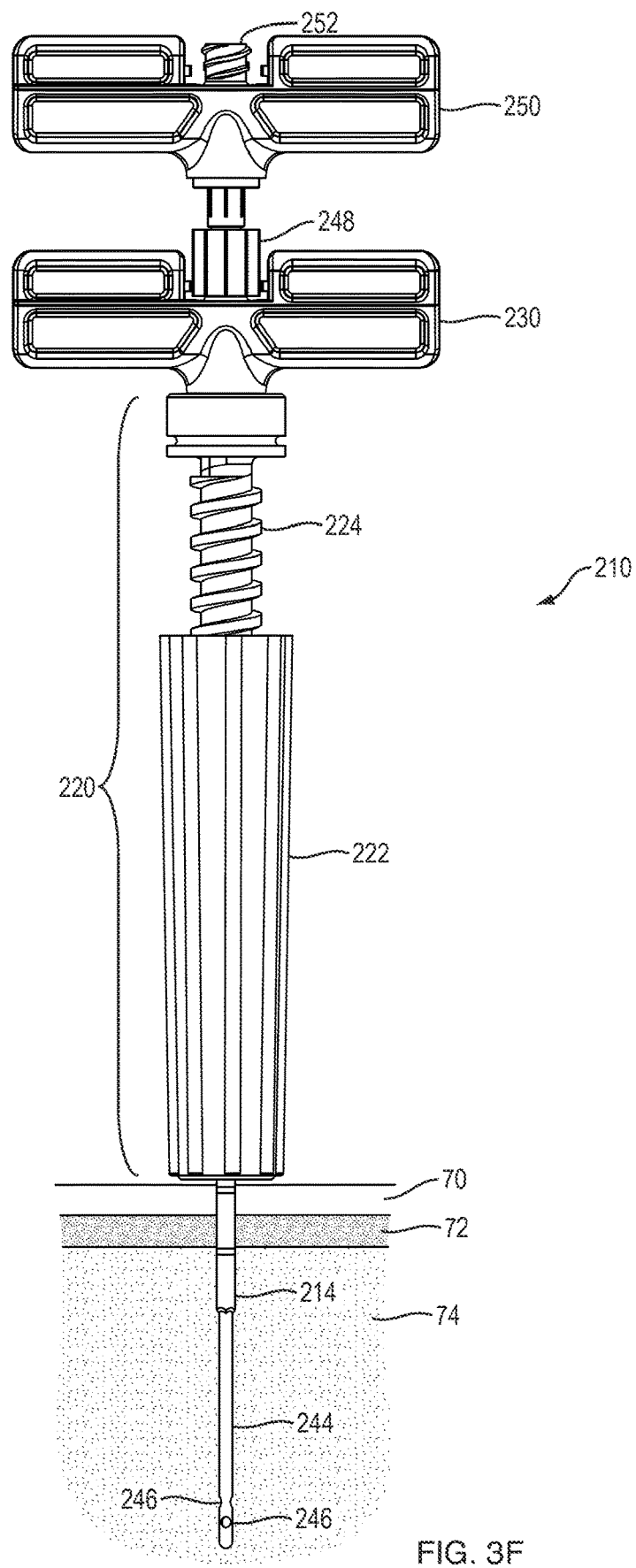
FIG. 3F illustrates the aspiration device of FIG. 3E with the aspiration cannula been inserted through the introducer cannula and into bone.

In FIG. 3F, the aspiration cannula 244 has been inserted through the introducer cannula 214 and into bone marrow 74. The screw mechanism 220, with leverage on the patient, allows the two assemblies (introducer 212 and aspiration 242) to be coupled by turning the lower (introducer) handle 230 counter clockwise, which causes introducer assembly to rise up toward the aspiration assembly. Once the two handles 230 and 250 meet and the assemblies are coupled through connector 248, continuing to turn the introducer handle 230 counter clockwise will cause both cannulae 214 and 244 to rise together out of the body.

Figure 3G:
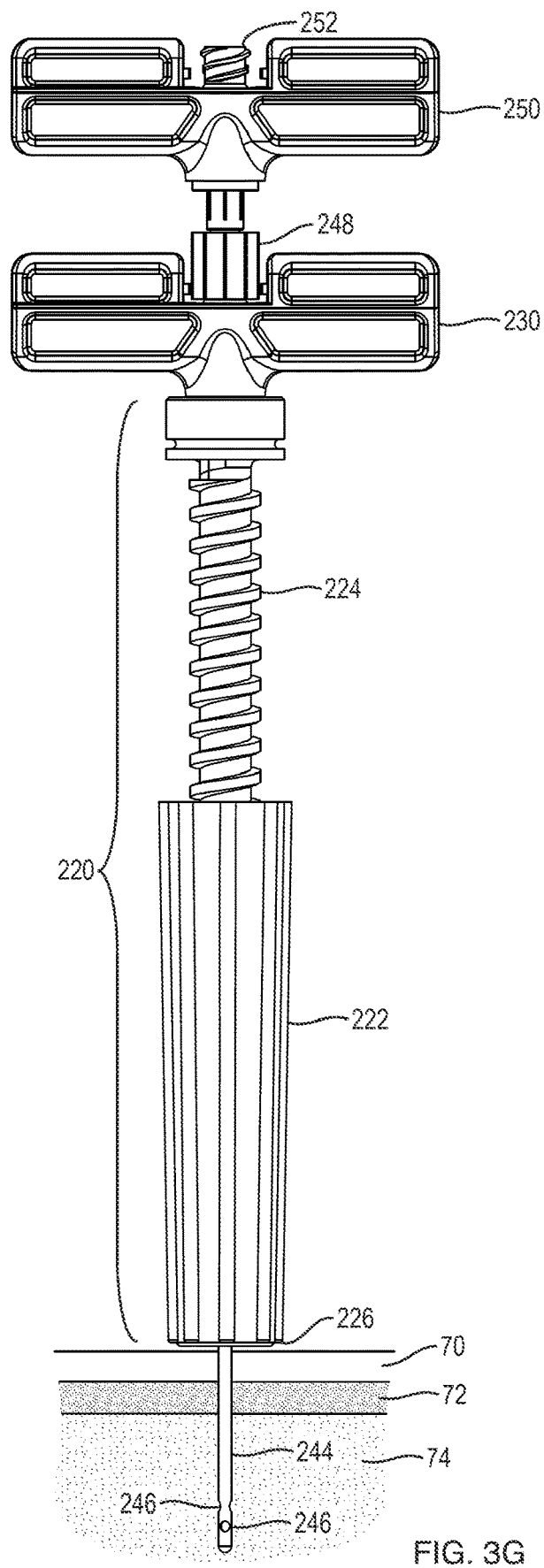
FIG. 3G illustrates the aspiration cannula of FIG. 3F partially withdrawn from bone and introducer cannula completely withdrawn from the bone with extension of the guide mechanism.

In FIG. 3G, the aspiration cannula 244 has been partially withdrawn from bone with extension of the guide mechanism 220. The introducer cannula 214, which is not visible in FIG. 3G, has been completely withdrawn from the bone and into the jacket 222 of the mechanism 220. Here, the turning of the introducer handle 230, and connected lead screw 224, in a counter clockwise direction lifts both cannulae together from the body. The introducer handle 230, the jacket 222 and the screw 224 act like a jack. Turning the handle 230 raises the jack which, because the handle 230 is engaged to the aspiration handle 250 by connector 248, moves both cannulae 214 and 244 together and out of the body.

Returning to FIG. 3D, features of the screw set employed in the embodiments will be described that allow precise changes in the depth of a cannula across a larger geography as it is retracted from the body. As shown in section view in FIG. 3D, the length of travel between lead screw 224 and jacket 222 is indicated as length T, which, in this example, is substantially the length of the threaded portion of the screw 224. The threaded portion of screw 224 engages with a threaded portion 223 of jacket 222. The distance (length) that the introducer cannula can extend beyond the distal end 226 when the screw mechanism is fully retracted is indicated as distance A. The distance (length) that the aspiration cannula 244 extends beyond the distal end 218 is shown as distance B.

Combinations of lengths and travel distances that have been found useful are described with reference to mechanism 220 of FIG. 3D but are also applicable to mechanisms 20, 120, 320, 420 and 520. Suitable combinations include:

a) The length of the lead screw is at least about 1.5 inches. From a practical perspective, a screw length of over 5 inches would be overly cumbersome. In FIG. 3D, the length of the travel T of the outer jacket of the screw mechanism is substantially equal to the length of the screw. When the screw length is at 1.5 inches, the jacket can travel about 1.5 inches relative to the screw, exposing or covering the introducer cannula in the process. The length of exposed cannula, of course, depends on the length of the cannula.

b) The screw mechanism in its fully retracted position will leave the maximum length of cannula exposed from the distal end of the mechanism (maximum exposed length). The screw mechanism in its fully extended position will leave the shortest length of the cannula exposed from the distal end of the mechanism (minimum exposed length). In the case where an aspiration cannula is inserted through an introducer cannula, the length of the two cannulae assembled and extending beyond the distal end of the screw mechanism defines the maximum and minimum exposed length. In FIG. 3D, the maximum exposed length of the introducer cannula alone is A, the maximum exposed length with the aspiration cannula added is A+B. The maximum exposed length when the screw mechanism is in a fully retracted position can be at least 50% and not greater than 200% of the length of travel of the screw relative to the jacket. Table 1 documents preferred, upper and lower maximum exposed lengths for different lengths of travel, e.g., different screw lengths.

TABLE 1

| Description | | Screw length | | | |
|---|---|---|---|---|---|
| | | 1.5 | 2 | 3 | 4 |
| Screw Length and Maximum Exposed Length (inches) | | | | | |
| lower range | Maximum exposed length | 0.75 | 1 | 1.5 | 2 |
| Preferred | Maximum exposed length | 2 | 2.5 | 3.5 | 4.5 |
| upper range | Maximum exposed length | 3 | 3.5 | 5.5 | 7.25 |
| Maximum Exposed Length as a percentage of Screw Length With Screw Guide Fully Retracted | | | | | |
| lower range | Maximum exposed length | 50% | 50% | 50% | 50% |
| Preferred | Maximum exposed length | 133% | 125% | 117% | 113% |
| upper range | Maximum exposed length | 200% | 175% | 183% | 181% |

Because the screw mechanism is used to set the depth of the cannula upon extraction using the patient as leverage, the length of the lead screw preferably has sufficient travel to anchor against the patient (to allow for the outer jacket to be screwed down against patient after the cannula is inserted into bone). The length of the screw preferably has sufficient travel to extract the needle from the bone. The parameters of the screw being at least 1.5 inches and the ratio of the screw to the overall "maximum exposed length" can accommodate different bone types and different sizes of patients (e.g., can accommodate for differing amounts of flesh over the bone of the patient).

Needles that have a screw mechanism on a first needle are designed to just control depth of entry and so any screw of such a mechanism is typically less than 1.5 inches in length and the ratio of screw length to length of exposed needle, when the jacket is in its fully retracted position, would not be expected to be within the range described above.

Traditional depth guides on marrow needles have a short travel distance associated with the screw mechanism, typically 1 inch or less. They are typically used only to set a depth of insertion and are not designed to control changes in depth as the marrow needle is retracted from the body. The threads used on traditional depth guides are fine so as to make small adjustment in penetration depth. These depth guides are typically provided on needles that are inserted into the vertebral body of the spine to make pilot holes for screws.

In embodiment of the present inventions, the combination of the screw set (e.g., 20, 120, 220, 320, 420, 520) and cannula (e.g., 14, 114, 214, 314, 414, 514) of the aspiration device allows the clinician to insert the cannula to a desired depth that can be adjusted during insertion. Once the depth is achieved, the aspiration device is secured against the patient by turning the screw set counterclockwise so that the outer jacket is snug to the patient skin. In certain embodiments, an aspiration cannula is inserted that has a blunt tip and side ports only. This aspiration cannula is secured to the introducer cannula in an air-tight manner using a connector, to seal against air flow through the introducer cannula. The connector can be a Luer-type connector and can include a hollow guide through which the aspiration cannula fits, the guide being inside a threaded tube, the threaded tube configured to attach to the threaded mechanism of a port on the introducer handle, as previously described. The aspiration cannula can be substantially longer than the introducer needle. Aspiration can occur at different locations (depths) as the cannula is, or cannulae are, moved proximally or distally within bone. For example, the cannula can be retracted by turning the screw set counter clockwise to position the cannula at a new location with each turn. In some embodiments, aspiration occurs from the side holes only.

FIG. 4 illustrates a sharp stylet 336 having handle 338 and a blunt stylet 356 having handle 345 for use with embodiments of the present invention. For each embodiment, the introducer cannula that breaks through the bone cortex with a sharp stylet, such as stylet 336 can also have with it a complimentary blunt tip stylet, such as stylet 356. Once the cannula has passed the cortex, some clinicians prefer to advance further into the bone space with a blunt tipped stylet to avoid having the introducer cannula come out through the cortex on the other side of the bone. A blunt stylet, or blunt cannula, is more likely to deflect along the inner wall of bone cortex. The embodiment illustrated in FIG. 5, for example, can benefit from a blunt stylet even though the device's cannula has a closed distal end. The blunt stylet is used to strengthen the introducer cannula and to prevent debris from clogging up the one more side holes.

Figure 5:
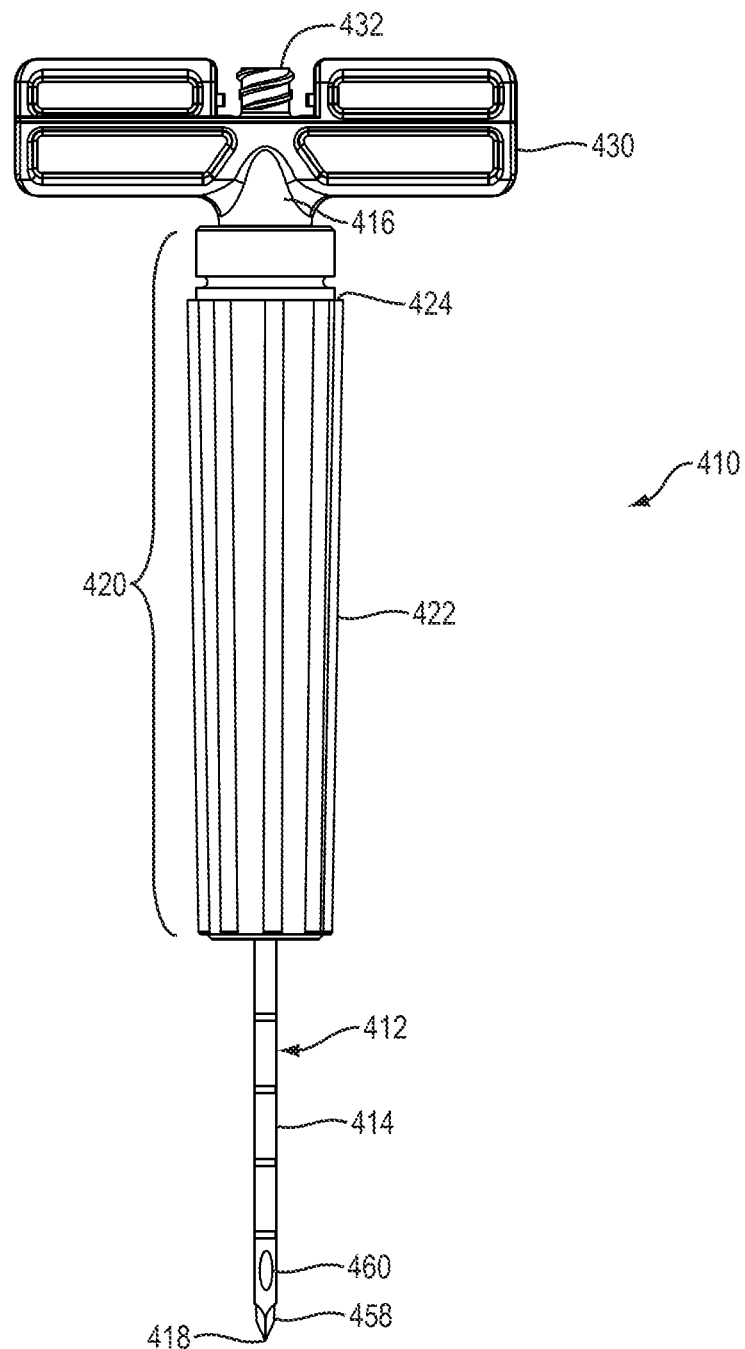
FIG. 5 illustrates an alternative aspiration device including an introducer cannula having a solid tip and a side hole.

FIG. 5 illustrates an alternative aspiration device 410 including an introducer cannula 414 having a solid tip 458 and one or more side holes (side ports) 460. The aspiration device 410 is similar to the aspiration device 10 of FIGS. 1A-1E. Similar features are designated using like reference numbers, but increased by 400. With respect to such similar features, the above description of device 10 also applies to the device 410.

As with aspiration device 10, the aspiration device 410 generally includes an introducer assembly 412 with handle 430 and port 432, an introducer cannula 414 with proximal and distal ends 416 and 418, respectively, and a mechanism 420 that includes threaded jacket 422 and lead screw 424 (inside jacket 422, but see lead screw 24 of FIG. 1B). Unlike the device 10, the device 410 does not include an open distal end at the introducer cannula for aspirating bone marrow, but instead includes a solid, sharp tip 458 at the distal end and a side hole 460 in the introducer cannula. Although only one side hole is shown in FIG. 5, the cannula can include multiple side holes. Aspiration is through the side hole(s) 460. During insertion into bone, a blunt stylet, such as stylet 356 of FIG. 4, can be inserted through port 432 into the lumen of the introducer cannula 414 to close off the one or more side holes 460.

An additional bone marrow aspiration device 510 is illustrated in FIGS. 6A-6B. The aspiration device 510 is similar to the aspiration device 210. Similar features are designated using like reference numbers, but increased by 300. With regard to such similar features, the above description of device 210 also applies to the device 510.

As with aspiration device 210, the aspiration device 510 generally includes an introducer assembly 512 having handle 530 and port 532, an introducer cannula 514 with proximal and distal ends 516 and 518, respectively, and a mechanism 520 that includes threaded jacket 522 and lead screw 524 (inside jacket 522), as illustrated in FIG. 6A. As with device 210, the device 510 further includes a sharp stylet 536 having a handle 538 that interlocks with handle 530. The device 510 also includes an aspiration assembly 542 configured to couple to the introducer assembly 512 at port 532 through connector 540. The aspiration assembly 542 includes an aspiration cannula 544 with side ports 546. A connector 548 of assembly 542 is configured to cooperate with connector 540 of the introducer assembly to couple the assemblies together. A port 552 is provided for connecting a syringe or other device. As with the side ports of device 210, when the aspiration cannula 544 is fully inserted into the introducer cannula 514 and extends through the distal opening of the introducer cannula, the side ports 546 are positioned distal to the distal end 518 of the introducer cannula, as for example illustrated in FIG. 6B. The aspiration device 510 is provided with a handle 550 that includes winged portions. Also provided is a blunt stylet whose handle 554 can interlock with the handle 550 of the aspiration assembly.

Figure 7B:
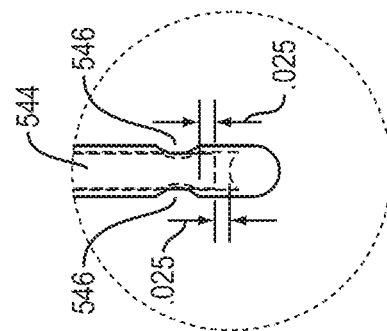
FIG. 7B is a detailed view of the tip of the aspiration assembly of FIG. 6B.
Figure 7A:
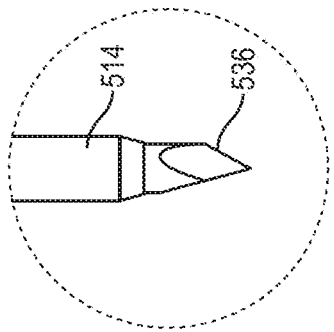
FIG. 7A is a detailed view of the tip of the introducer assembly of FIG. 6A.

FIG. 7A provides detail view of the distal end of introducer assembly 512 of FIG. 6A illustrating the sharp stylet 536 extending beyond the distal end of the introducer cannula 514. FIG. 7B provides a detail view of the distal end of the aspiration cannula 544 of FIG. 6B illustrating the two side ports 546 offset from the closed, distal end of the aspiration cannula.

Device 510 differs from device 210 in the configuration of the distal end 526 of the jacket 522. The jacket 522 tapers at the distal end 528 and defines a smaller surface 528 for contacting the skin of the patient as compared to relative large contact surface 228 of device 210 (see, e.g., FIG. 3D). In the particular example, the introducer cannula is an 11 Gauge cannula that extends 1.676 inches beyond the distal end of the jacket 522 when the mechanism 520 is in a retracted position, as shown in FIG. 6A. The length of the retracted mechanism is 4.250 inches. The aspiration cannula, which is a 14 Gauge cannula, extends 3.250 inches beyond the distal end 518 of the introducer cannula, as shown in FIG. 6B.

Use of device 510 of FIGS. 6A-6B for extracting bone marrow is substantially the same that of device 210 described above with reference to FIGS. 3A-3G.

Embodiments have been described that can be used to aspirate material, e.g., bone marrow, by placing the cannula a certain distance into the patient and then aspirating in different locations along the trajectory as the cannula is pulled proximally (from the body) with the screw mechanism, e.g., by unwinding the handle of the aspiration device, and with leverage against the patient. Using the same screw mechanism, one can aspirate moving the cannula distally (into the body), while using the patient as the stop and then using the screw mechanism to retrieve the cannula upon completion of the aspirate.

Aspirating while advancing the cannula is described with reference to the embodiment of FIGS. 3A-3D. First, one can insert the introducer cannula 214 past the cortex into bone marrow with the sharp stylet 236 in place. Once past the cortex, one can remove the sharp stylet and screw the jacket 222 down to patient's skin. Next, one can insert in the blunt tipped aspiration cannula 244 through the introducer cannula 214. The aspiration cannula is longer, e.g., 1.5 inches longer, than the introducer cannula. Since the inner "spongy bone" is still quite rigid, the handle of the aspiration cannula 244 will likely stop at about 1.5 inches above the introducer handle 230 and its distal end dead end at the distal end of the introducer cannula inside the body. Holding the outer jacket 222 of the screw set 220 with one hand one can turn the introducer handle 230 counter clockwise until the handle rises up the approximate 1.5 inches and can connect to the handle 250 of the aspiration cannula. At this point, the introducer cannula 214 may be out of the body, positioned under the extended screw set, and only the aspiration cannula 244 will be a short distance into the body. In other words, the introducer cannula slides over the aspiration cannula, but the aspiration cannula does not move because it is not connected to the introducer cannula.

At this point, one can connect a syringe to port 252 and aspirate 1 mL of aspirate. This first volume of aspirate is at the top of the trajectory into the bone. Then, one can turn the jacket 222 of the screw set counter clockwise by 360 degrees. This will cause the screw set 220 to rise above the patient a short distance. Then, preferably using a mallet, one can tap both of the cannulae forward until the surface 226 of outer screw jacket 222 touches the patient. The cannulae will advance the distance the jacket 222 is above the patient based on turning the jacket 360 degrees. Now, one can connect a syringe and aspirate another 1 mL of marrow, the second volume of aspirate in the trajectory. Next, one can disconnect the syringe, turn the jacket 360 degrees to rise it above the patient, tap the two cannulae forward until the screw jacket 222 is flush with patient, re-connect the syringe, and draw 1 mL. This can be repeated until one has obtained the desired volume of aspirate or one runs out of screw length.

Aspirating while advancing the cannulae can be accomplished with the embodiment of FIGS. 2A-2B by having the second cannula 144 closing off the open lumen of the first cannula 114. Aspiration can occur through a cut out made in both cannulae at their distal ends, the cut outs lining up to create a fluid path. Alternatively, the second cannula 144 can protrude slightly beyond the first cannula 114 and have side ports.

One can also accomplish aspiration, when advancing the cannula with the screw set into bone, using embodiments that do not include a second, aspiration cannula. Preferably, one employs an aspiration device, such as device 410, where the distal end is permanently closed with a sharp point. If an aspiration device, such as device 10, is used, where the end of the introducer cannula has an open distal end after removing the sharp stylet, one would have to put in a stylet every time the cannula is advanced into bone. This is so, because advancing an open lumen cannula into bone is not desirable, as the cannula will likely clog, which will diminish, if not prevent, the ability to aspirate through the cannula.

In any case, when aspirating as one advance the cannula, as opposed to as one retracts, the introducer cannula, in the preferred embodiment, has a closed off end with a sharp point. Alternatively, one can close off the cannula with a second cannula that is preferably blunt. The first cannula has a screw set. One can use the screw set as a guide to advance the cannula, or cannulae, only a certain distance based on the distance between the screw set and the patient, which is based on each 360 degree counter clockwise turn of the jacket. Aspiration can occur at each location as the cannula is advanced.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of aspirating bone marrow, the method comprising:
    positioning an introducer cannula of an introducer assembly in bone of a patient at a first depth within the bone;
    aspirating bone marrow through a lumen of the introducer cannula positioned at the first depth;
    with a mechanism at the introducer assembly, moving the introducer cannula within the bone with leverage on the patient to a second depth different from the first depth; and
    aspirating bone marrow through the lumen of the introducer cannula positioned at the second depth.

2. The method of claim 1, wherein the bone marrow is aspirated while the introducer cannula is moved with the mechanism.

3. The method of claim 1, wherein the mechanism comprises a screw assembly, the screw assembly including a threaded jacket and a lead screw receivable in the threaded jacket, at least a portion of the introducer cannula extending through the lead screw.

4. The method of claim 3, further comprising contacting the patient with a surface of the threaded jacket to provide the leverage.

5. The method of claim 3, further comprising adjusting a length of the introducer cannula that extends from a distal end of the threaded jacket by advancing the lead screw into the threaded jacket or reversing the lead screw out of the threaded jacket.

6. The method of claim 3, further comprising inserting an aspiration cannula through the lumen of the introducer cannula, the aspiration cannula extending beyond a distal end of the introducer cannula, and wherein the bone marrow is aspirated with the aspiration cannula.

7. The method of claim 6, further comprising coupling the aspiration cannula to the introducer assembly with a connector.

8. The method of claim 7, wherein coupling the aspiration cannula to the introducer assembly includes forming an air-tight seal between the aspiration cannula and the introducer assembly to seal against air flow through the introducer cannula.

9. The method of claim 7, wherein moving the introducer cannula with the mechanism includes moving the introducer cannula and the aspiration cannula in tandem relative to the threaded jacket.

10. The method of claim 9, wherein the introducer cannula and the aspiration cannula move without relative rotation to each other when moved by the mechanism.

11. The method of claim 1, wherein the introducer cannula includes a solid and sharp distal end.

12. The method of claim 11, wherein aspirating the bone marrow includes aspirating through one or more side ports in the introducer cannula.

13. The method of claim 1, wherein aspirating the bone marrow includes aspirating at depths within the bone different from the first and second depths.

14. A method of aspirating bone marrow, the method comprising:
- inserting an aspiration cannula through an introducer cannula of an introducer assembly, the introducer cannula positioned in bone of a patient at a first depth within the bone, the aspiration cannula extending beyond a distal end of the introducer cannula;
- aspirating bone marrow through a port in the aspiration cannula, the port being distal to the distal end of the introducer cannula positioned at the first depth;
- with a mechanism at the introducer assembly, moving the introducer cannula and the aspiration cannula in tandem within the bone with leverage on the patient, to position the introducer cannula at a second depth different from the first depth; and
- aspirating bone marrow through the port in the aspiration cannula, the port being distal to the distal end of the introducer cannula positioned at the second depth.

15. The method of claim 14, further comprising coupling the aspiration cannula to the introducer assembly with a connector and forming an air-tight seal between the aspiration cannula and the introducer cannula to seal against air flow through the introducer cannula.

16. The method of claim 15, wherein the mechanism comprises a screw assembly, the screw assembly including a threaded jacket and a lead screw receivable in the threaded jacket, at least a portion of the introducer cannula extending through the lead screw.

17. The method of claim 16, further comprising contacting the patient with a surface of the threaded jacket to provide the leverage.

18. The method of claim 17, further comprising adjusting a length of the aspiration cannula that extends beyond a distal end of the threaded jacket by advancing the lead screw into the threaded jacket or reversing the lead screw out of the threaded jacket.

19. The method of claim 14, wherein aspirating the bone marrow includes aspirating at depths within the bone different from the first and second depths.

* * * * *